(12) United States Patent
Shelton, IV et al.

(10) Patent No.: US 12,127,741 B2
(45) Date of Patent: Oct. 29, 2024

(54) STAPLE CARTRIDGES COMPRISING DRIVER ARRANGEMENTS

(71) Applicant: Cilag GmbH International, Zug (CH)

(72) Inventors: Frederick E. Shelton, IV, Hillsboro, OH (US); Jerome R. Morgan, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/388,402

(22) Filed: Nov. 9, 2023

(65) Prior Publication Data

US 2024/0065691 A1 Feb. 29, 2024

Related U.S. Application Data

(63) Continuation of application No. 17/582,137, filed on Jan. 24, 2022, now Pat. No. 11,864,760, which is a continuation of application No. 16/587,452, filed on Sep. 30, 2019, now Pat. No. 11,241,229, which is a continuation of application No. 14/527,398, filed on Oct. 29, 2014, now Pat. No. 11,141,153.

(51) Int. Cl.
*A61B 17/064* (2006.01)
*A61B 17/072* (2006.01)

(52) U.S. Cl.
CPC ........... *A61B 17/07207* (2013.01); *A61B 2017/07228* (2013.01); *A61B 2017/07235* (2013.01); *A61B 2017/07271* (2013.01); *A61B 2017/07278* (2013.01)

(58) Field of Classification Search
CPC .......................... A61B 17/072; A61B 17/0727
See application file for complete search history.

(56) References Cited

U.S. PATENT DOCUMENTS

| | | |
|---|---|---|
| D278,081 S | 3/1985 | Green |
| 4,955,959 A | 9/1990 | Tompkins et al. |
| 4,978,049 A | 12/1990 | Green |
| 5,395,034 A | 3/1995 | Allen et al. |
| 5,403,312 A | 4/1995 | Yates et al. |
| 5,630,541 A | 5/1997 | Williamson, IV et al. |
| 5,662,258 A | 9/1997 | Knodel et al. |
| 6,131,789 A | 10/2000 | Schulze et al. |
| 6,669,073 B2 | 12/2003 | Milliman et al. |
| 6,978,921 B2 | 12/2005 | Shelton, IV et al. |
| 7,000,818 B2 | 2/2006 | Shelton, IV et al. |
| 7,044,352 B2 | 5/2006 | Shelton, IV et al. |
| 7,143,923 B2 | 12/2006 | Shelton, IV et al. |
| 7,398,908 B2 | 7/2008 | Holsten et al. |
| 7,422,139 B2 | 9/2008 | Shelton, IV et al. |
| 7,438,209 B1 | 10/2008 | Hess et al. |
| 7,464,849 B2 | 12/2008 | Shelton, IV et al. |
| 7,670,334 B2 | 3/2010 | Hueil et al. |
| 7,753,245 B2 | 7/2010 | Boudreaux et al. |
| 7,794,475 B2 | 9/2010 | Hess et al. |
| 7,845,537 B2 | 12/2010 | Shelton, IV et al. |
| 7,934,630 B2 | 5/2011 | Shelton, IV et al. |
| 7,980,443 B2 | 7/2011 | Scheib et al. |
| 8,210,411 B2 | 7/2012 | Yates et al. |
| 8,220,688 B2 | 7/2012 | Laurent et al. |

(Continued)

*Primary Examiner* — Eyamindae C Jallow

(57) ABSTRACT

Staple cartridge assemblies are disclosed herein which are an improvement over previous staple cartridge assemblies. Certain embodiments utilize tri-staple drivers which simultaneously eject three staples from a staple cartridge.

20 Claims, 27 Drawing Sheets

(56) References Cited

U.S. PATENT DOCUMENTS

| | | |
|---|---|---|
| 8,308,040 B2 | 11/2012 | Huang et al. |
| 8,393,514 B2 | 3/2013 | Shelton, IV et al. |
| 8,496,154 B2 | 7/2013 | Marczyk et al. |
| 8,561,870 B2 | 10/2013 | Baxter, III et al. |
| 8,590,762 B2 | 11/2013 | Hess et al. |
| 8,608,045 B2 | 12/2013 | Smith et al. |
| 8,733,613 B2 | 5/2014 | Huitema et al. |
| 9,072,535 B2 | 7/2015 | Shelton, IV et al. |
| 9,101,358 B2 | 8/2015 | Kerr et al. |
| 9,345,481 B2 | 5/2016 | Hall et al. |
| 9,386,984 B2 | 7/2016 | Aronhalt et al. |
| 9,498,213 B2 | 11/2016 | Marczyk et al. |
| 9,839,420 B2 | 12/2017 | Shelton, IV et al. |
| 10,194,910 B2 | 2/2019 | Shelton, IV et al. |
| 10,285,700 B2 | 5/2019 | Scheib |
| 10,517,594 B2 * | 12/2019 | Shelton, IV ..... A61B 17/07207 |
| 10,631,857 B2 | 4/2020 | Kostrzewski |
| 11,141,153 B2 | 10/2021 | Shelton, IV et al. |
| 11,241,229 B2 | 2/2022 | Shelton, IV et al. |
| 11,864,760 B2 | 1/2024 | Shelton, IV et al. |
| 2006/0180634 A1 | 8/2006 | Shelton et al. |
| 2007/0175955 A1 | 8/2007 | Shelton et al. |
| 2014/0166724 A1 | 6/2014 | Schellin et al. |
| 2014/0166725 A1 | 6/2014 | Schellin et al. |
| 2014/0263552 A1 | 9/2014 | Hall et al. |
| 2015/0327862 A1 * | 11/2015 | Kostrzewski .... A61B 17/07207 227/178.1 |
| 2015/0335328 A1 * | 11/2015 | Shelton, IV ......... A61B 17/064 227/177.1 |

\* cited by examiner

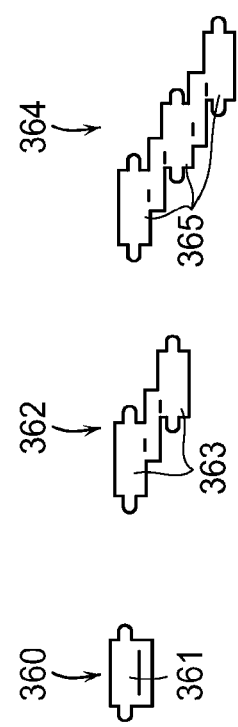
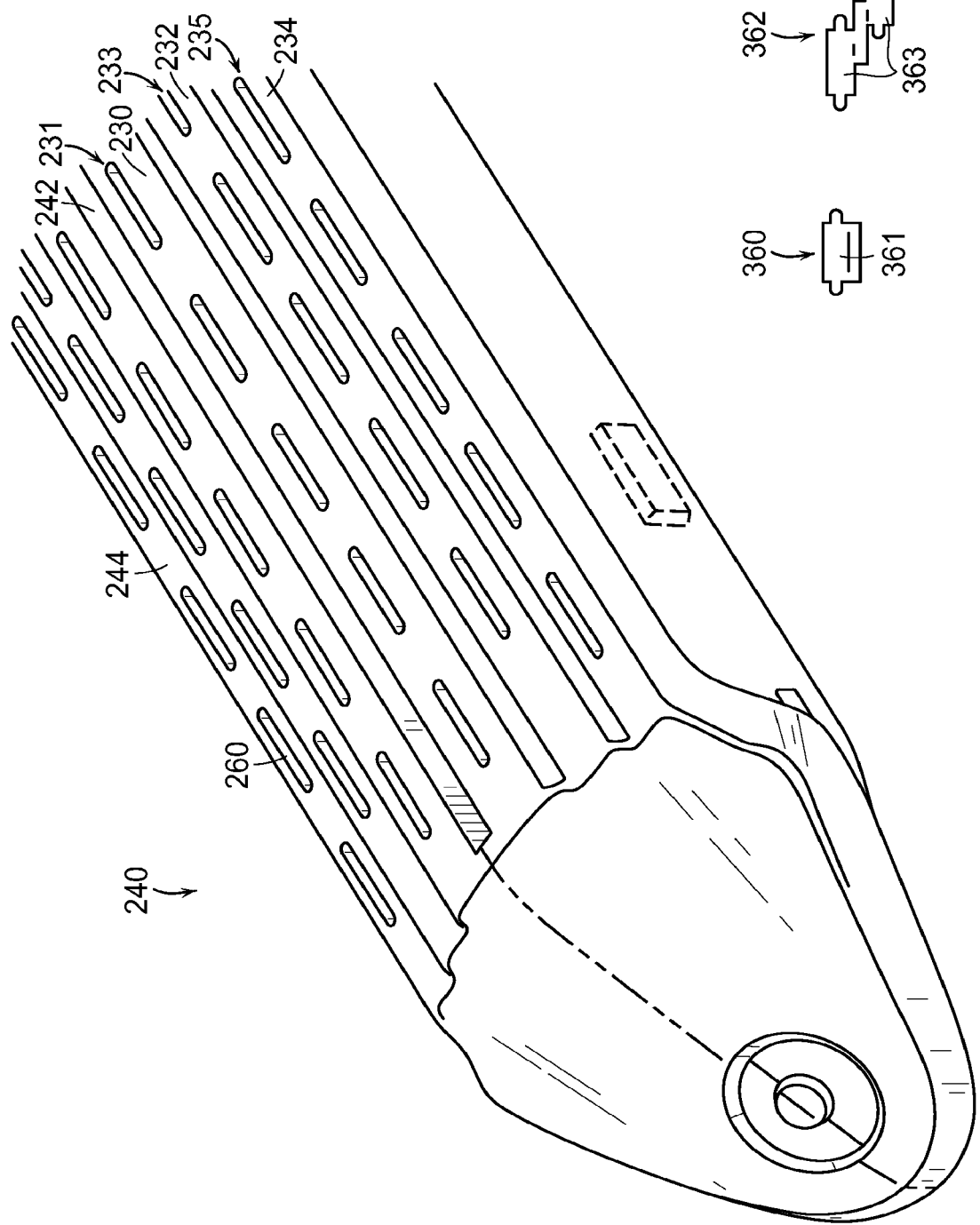
FIG. 3
FIG. 4

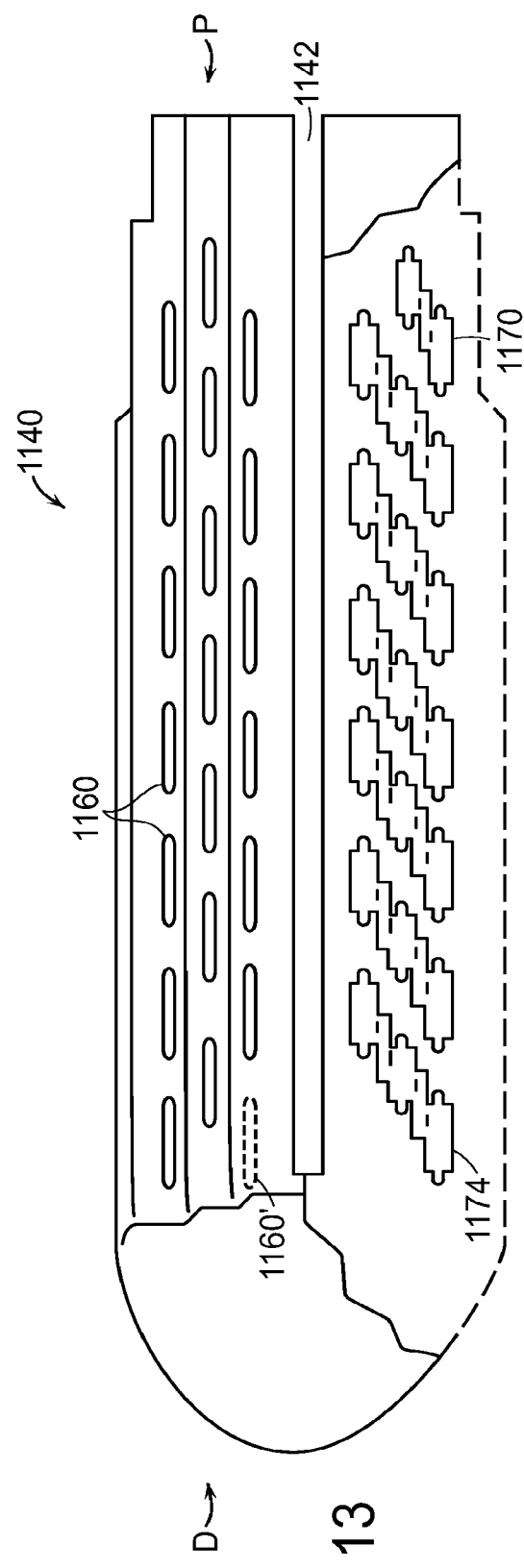
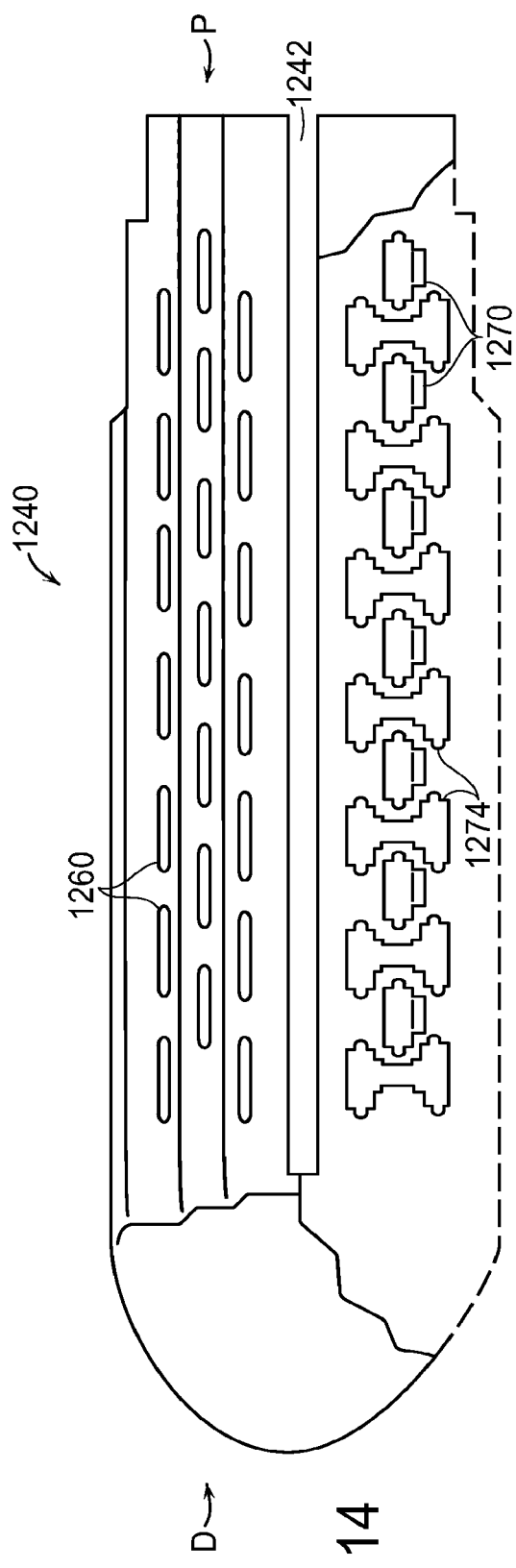

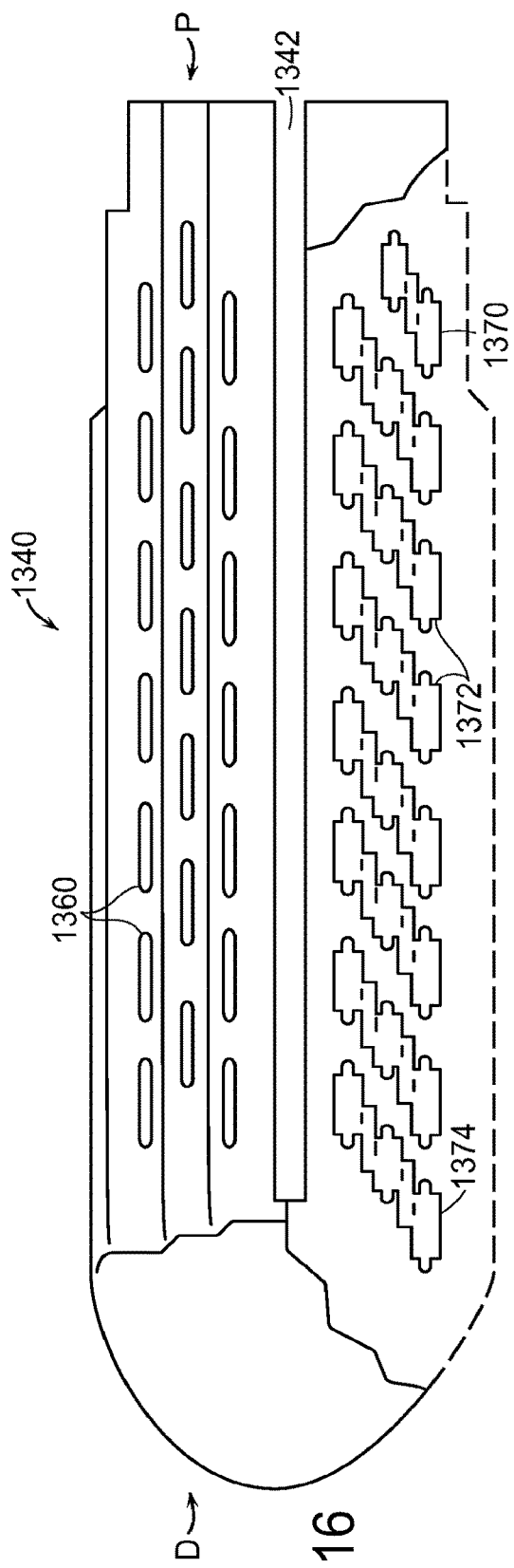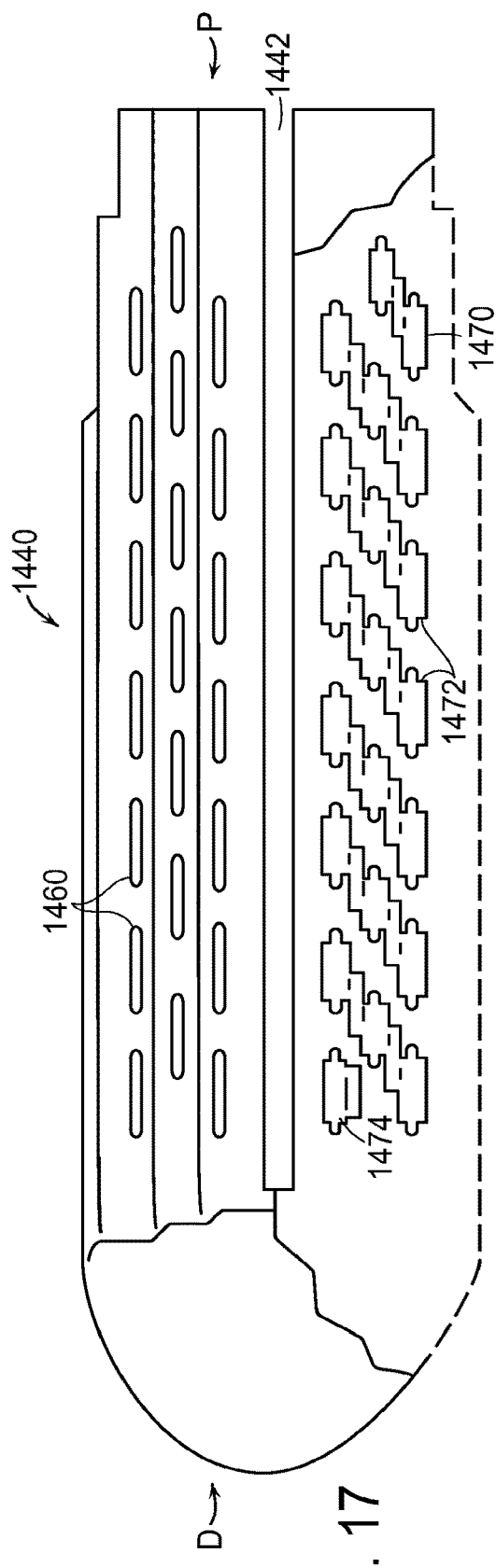

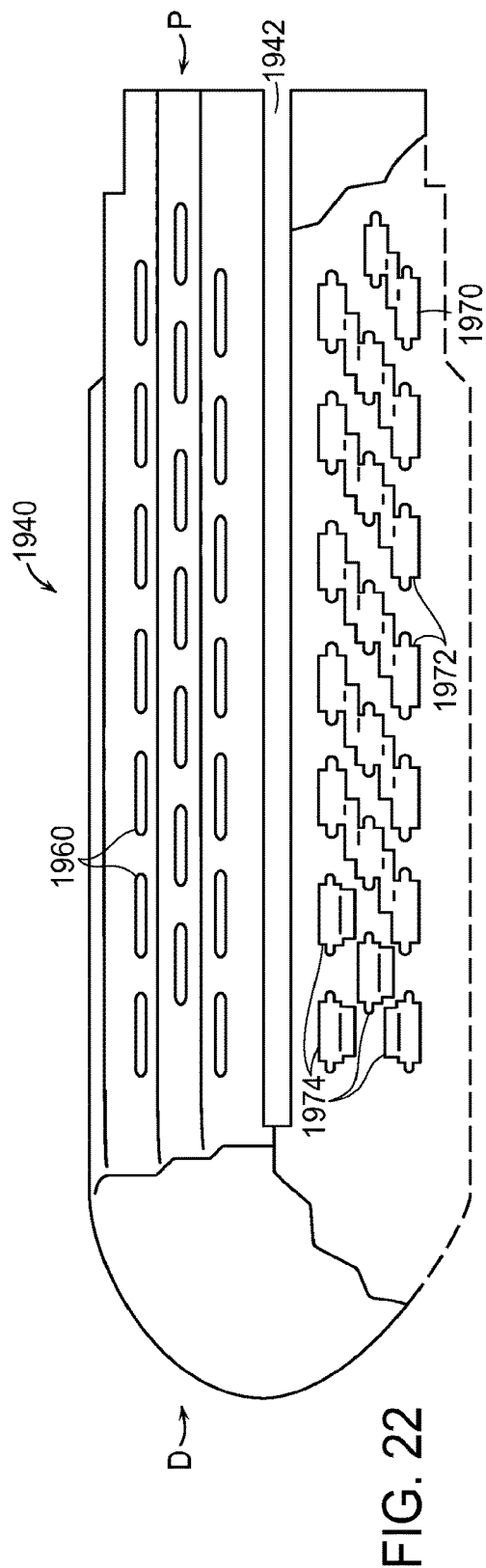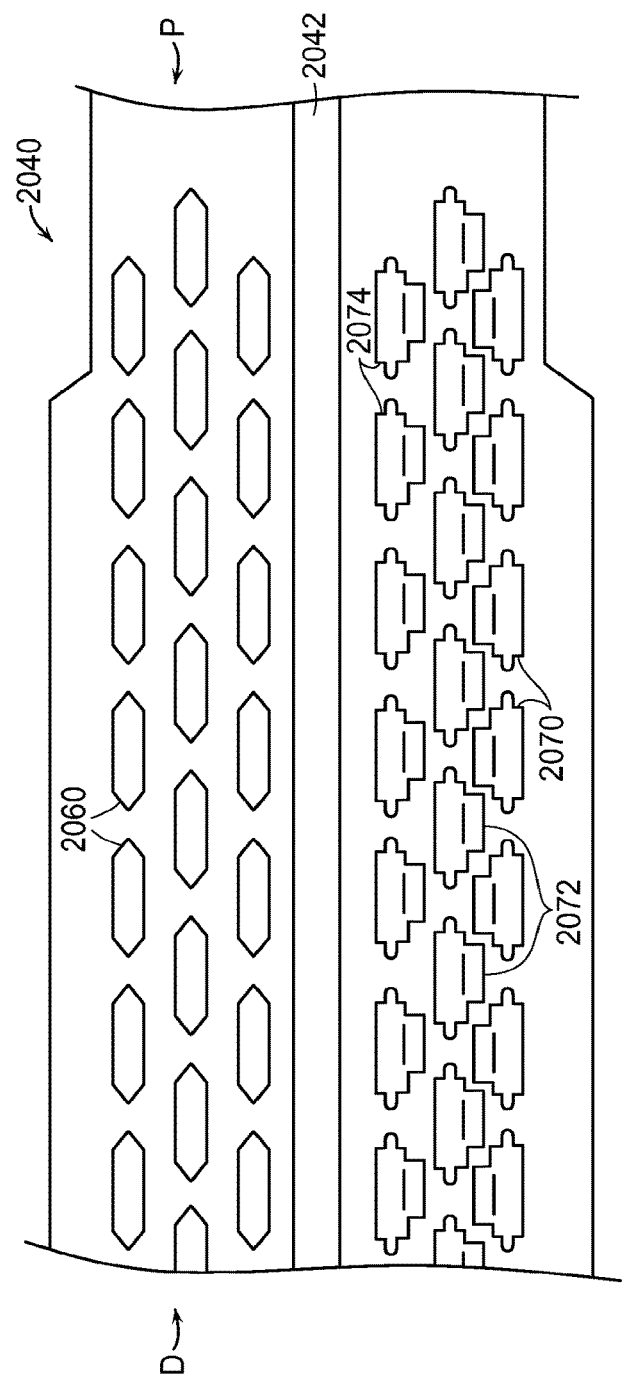

STAPLE CARTRIDGES COMPRISING DRIVER ARRANGEMENTS

CROSS-REFERENCE TO RELATED APPLICATIONS

This application is a continuation application claiming priority under 35 U.S.C. § 120 to U.S. patent application Ser. No. 17/582,137, entitled STAPLE CARTRIDGES COMPRISING DRIVER ARRANGEMENTS, filed Jan. 24, 2022, which issued on Jan. 9, 2024 as U.S. Pat. No. 11,864,760, which is a continuation application claiming priority under 35 U.S.C. § 120 to U.S. patent application Ser. No. 16/587,452, entitled STAPLE CARTRIDGES COMPRISING DRIVER ARRANGEMENTS, filed Sep. 30, 2019, which issued on Feb. 8, 2022 as U.S. Pat. No. 11,241,229, which is a continuation application claiming priority under 35 U.S.C. § 120 to U.S. patent application Ser. No. 14/527,398, entitled STAPLE CARTRIDGES COMPRISING DRIVER ARRANGEMENTS, filed Oct. 29, 2014, which issued on Oct. 12, 2021 as U.S. Pat. No. 11,141,153, the entire disclosures of which are incorporated by reference in their entireties herein.

BACKGROUND

The present invention relates to stapling instruments and, in various embodiments, to a surgical stapling instrument for producing one or more rows of staples.

A stapling instrument can include a pair of cooperating elongate jaw members, wherein each jaw member can be adapted to be inserted into a patient and positioned relative to tissue that is to be stapled and/or incised. In various embodiments, one of the jaw members can support a staple cartridge with at least two laterally spaced rows of staples contained therein, and the other jaw member can support an anvil with staple-forming pockets aligned with the rows of staples in the staple cartridge. Generally, the stapling instrument can further include a pusher bar and a knife blade which are slidable relative to the jaw members to sequentially eject the staples from the staple cartridge via camming surfaces on the pusher bar and/or camming surfaces on a wedge sled that is pushed by the pusher bar. In at least one embodiment, the camming surfaces can be configured to activate a plurality of staple drivers carried by the cartridge and associated with the staples in order to push the staples against the anvil and form laterally spaced rows of deformed staples in the tissue gripped between the jaw members. In at least one embodiment, the knife blade can trail the camming surfaces and cut the tissue along a line between the staple rows. Examples of such stapling instruments are disclosed in U.S. Pat. No. 7,794,475, entitled SURGICAL STAPLES HAVING COMPRESSIBLE OR CRUSHABLE MEMBERS FOR SECURING TISSUE THEREIN AND STAPLING INSTRUMENTS FOR DEPLOYING THE SAME, the entire disclosure of which is hereby incorporated by reference herein.

BRIEF DESCRIPTION OF THE DRAWINGS

Various features of the embodiments described herein are set forth with particularity in the appended claims. The various embodiments, however, both as to organization and methods of operation, together with advantages thereof, may be understood in accordance with the following description taken in conjunction with the accompanying drawings as follows:

FIG. 3 is a partial perspective view of a staple cartridge assembly for use with the surgical instrument of FIG. 1;

FIG. 4 is a top view of staple drivers for use with a staple cartridge assembly;

FIG. 13 is a top break-away view of a staple cartridge assembly comprising a driver arrangement;

FIG. 14 is a top break-away view of a staple cartridge assembly comprising a driver arrangement;

FIG. 16 is a top break-away view of a staple cartridge assembly comprising a driver arrangement;

FIG. 17 is a top break-away view of a staple cartridge assembly comprising a driver arrangement;

FIG. 22 is a top break-away view of a staple cartridge assembly comprising a driver arrangement;

FIG. 23 is a partial top break-away view of a staple cartridge assembly comprising a driver arrangement;

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
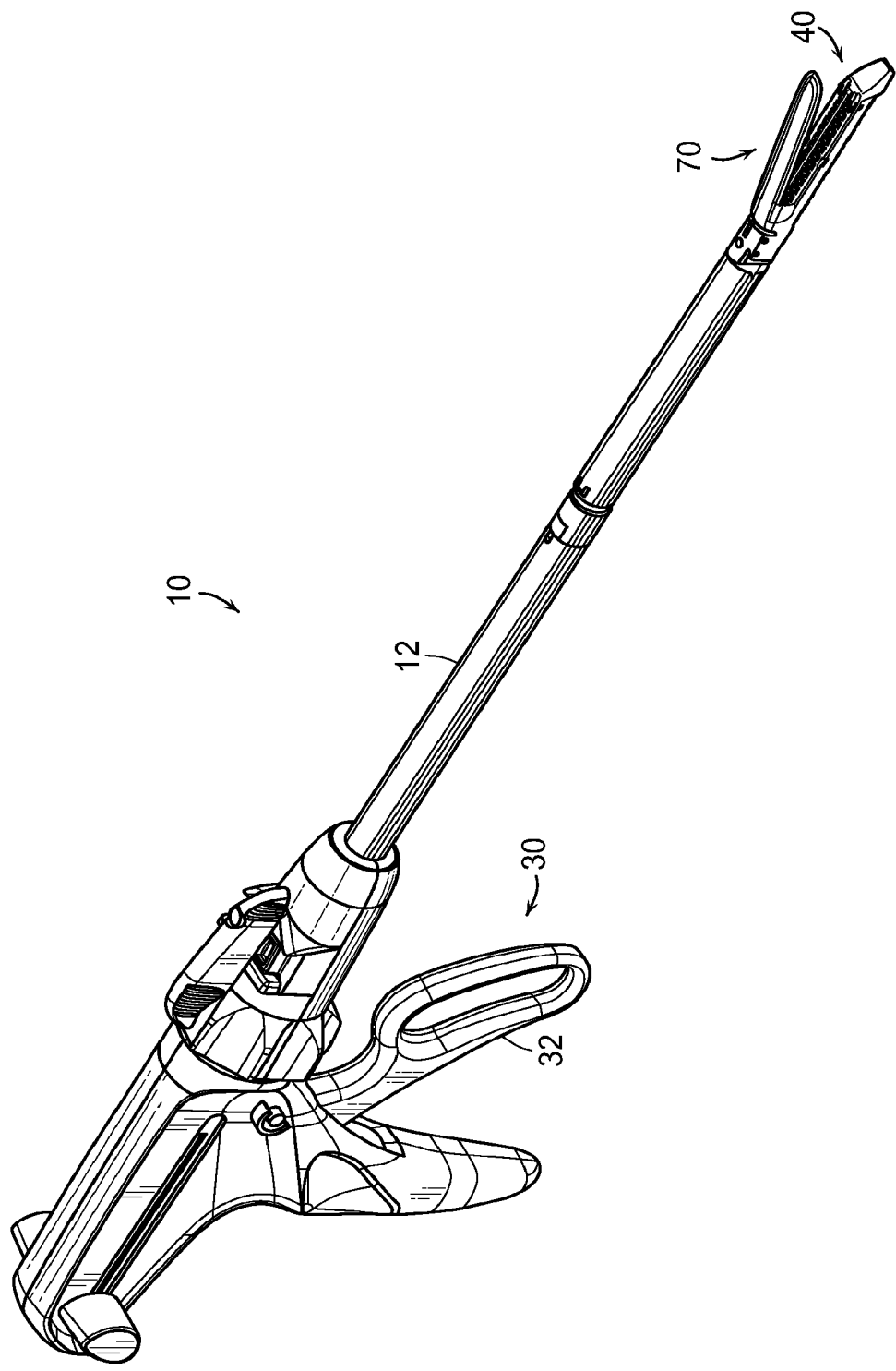
FIG. 1 is a perspective view of a surgical instrument.

Applicant of the present application owns the following patent application which was filed on Oct. 29, 2014 and which is herein incorporated by reference in its entirety:

U.S. patent application Ser. No. 14/527,384, entitled CARTRIDGE ASSEMBLIES FOR SURGICAL STAPLERS, now U.S. Patent Application Publication No. 2016/0120544.

Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the person of ordinary skill in the art will readily appreciate that the various methods and devices disclosed herein can be used in numerous surgical procedures and applications including, for example, in connection with open surgical procedures. As the present Detailed Description proceeds, those of ordinary skill in the art will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongated shaft of a surgical instrument can be advanced.

The present disclosure is directed toward a staple drive assembly for use in a staple cartridge. The staple drive assembly may also be used in a disposable loading unit and/or any other suitable device and can be configured to deploy numerous types of staples and/or fasteners. The staple drive assembly includes an actuation sled and at least one staple driver. The staple cartridge includes a tissue contacting and/or supporting surface having a number of staple cavities wherein each staple cavity is adapted for releasably receiving a staple. The staple cartridge may include a guide channel/knife slot extending from a proximal portion to a distal portion along its longitudinal axis. In one embodiment, the staple cartridge is adapted for use in a surgical stapler having a drive mechanism.

The actuation sled can include a base, at least one camming member and a guide member. Each camming member can include a first or leading cam wedge and a second or trailing cam wedge. The leading and trailing cam wedges can be laterally and longitudinally spaced apart from one another. Spacing of the cam wedges apart, both laterally and longitudinally, creates a situation in which the staple driver is contacted at points offset in two planes so that as the staple driver is driven, it is controlled and driven substantially perpendicular to the tissue plane of the cartridge without rocking in any direction which would compromise driving the staple perpendicular to the tissue contacting plane. Additionally, each cam wedge can include a first drive face and a second drive face. In one embodiment, the first drive faces form first drive angles with respect to the base and second drive faces form second drive angles with respect to a plane that is substantially parallel to the base. The guide member is adapted for slidably engaging the guide channel for aligning and guiding the actuation sled as it translates through the staple cartridge. While two drive faces are discussed herein, it is also within the scope of this disclosure to include various configurations of drive faces. For example, 1, 2, 3, 4, or more drive faces at various drive angles between 5° and 80° to enhance the firing of the staples may also be employed.

Each staple driver includes at least one driver plate or staple retaining features and at least one cam member. In one embodiment, each staple driver includes three driver plates and two cam members. Such staple drivers can be referred to as tri-staple drivers. In an alternate embodiment, each staple driver includes one driver plate and two cam members. In a further embodiment, each staple driver includes two driver plates and two cam members. First and second cam members are adapted for slidably engaging one of the cam assemblies of the actuation sled. Each cam member includes first and second cam surfaces that define respective first and second engagement or receiving angles that are complementary to the first and second drive angles. The first and second cam members can be longitudinally and laterally spaced apart to complement the arrangement of the leading and trailing cam wedges of the actuation sled. Additional combinations of cam members, receiving angles, and number of camming surfaces are within the scope of this disclosure and the ranges described above are inclusive of the values disclosed.

Distal travel of the actuation sled through the staple cartridge causes the sequential engagement of the actuation sled and the staple drivers disposed in the staple cartridge. As the actuation sled moves along the longitudinal axis of the staple cartridge, in various instances, the first drive faces slidably engage the first cam surfaces thereby urging each staple driver in a generally vertical direction. As the actuation sled continues to move distally, in various instances, the second drive faces slidably engage the second cam surfaces of each staple driver to continue to drive each staple driver in a generally vertical direction while the first drive faces disengage from the first cam surfaces. Also, in various instances, each camming member contacts each staple driver in at least two longitudinally spaced locations for urging each staple driver vertically. This longitudinally staggered arrangement of the drive faces in cooperation with the complementary staggered arrangement of the cam members can improve the longitudinal stability of the staple driver as it moves vertically. Additionally, the first and second drive angles in cooperation with the complementary first and second receiving angles can contribute to the improved longitudinal stability of each staple driver. In further embodiments, different arrangements and number of camming locations may be employed, such as 1, 2, 3, or more camming locations.

In a further embodiment of the present disclosure, an actuation sled includes first and second camming members, a base, and a guide member. Each camming member includes first and second cam wedges that are longitudinally spaced apart and define a drive angle with respect to the base. The first and second cam wedges of each camming member are laterally spaced apart as well.

Another embodiment of the present disclosure includes an actuation sled that includes first and second camming members, a base, and a guide member. Each camming member includes first and second cam wedges that are laterally spaced apart from each other and define a plurality of drive angles with respect to the base.

In yet another embodiment of the present disclosure, each of the described actuation sleds may be included at a distal end of a cam bar or actuation member in a surgical stapling apparatus.

In a further embodiment of the present disclosure, the staple drive assembly may include at least one proximal staple driver, at least one middle staple driver and at least one distal staple driver. The proximal staple driver is disposed at the proximal end of the staple cartridge and is adapted to eject the outermost, most proximal staple. The distal staple driver is positioned on the distal end of staple cartridge and is configured to eject the outermost, most distal staples. Each staple driver may have first and second cam members. In turn, each cam member may have at least one engagement surface. Additionally, the proximal staple driver has a single driver plate, the middle staple driver has at least three driver plates, which can be referred to as tri-staple drivers, and the distal staple driver has at least four driver plates.

The configuration of the staple drivers and the sequence of firing the staples disclosed herein can provide added benefits such as, for example, stabilization of the firing stroke as the actuation sled moves distally through the staple cartridge, reducing trauma to the engaged tissue, reducing the resistance of the articulation sled as it moves distally through the staple cartridge, and/or providing a marker to better align subsequent staple cartridges.

In a non-limiting embodiment of the present disclosure, each staple driver may be configured to engage and deploy one, two, three, four, five, or more staples. The specific configuration of these staple drivers and the sequence of deployment of the staples can be selected to provide unique benefits which will be discussed in greater detail below.

In a non-limiting embodiment of the present disclosure, the staple cartridge comprises a central longitudinal slot, or knife channel, permitting distal travel of a firing member. The firing member comprises a cutting member and an articulation sled. The firing member is configured to translate the staple cartridge longitudinally. The longitudinal translation of the firing member causes the actuation sled to engage the plurality of staple drivers as the firing member moves from a proximal-most position to a distal-most position. As the firing member translates distally, the cutting member dissects the engaged tissue. The staples are aligned in rows on each side of the longitudinal slot. On one side of the longitudinal slot, the staples are aligned in a first row of staples, a second row of staples and a third row of staples, wherein the first row of staples is positioned adjacent the longitudinal slot. As the firing member translates distally, the actuation sled engages the plurality of staple pushers to deploy the staples.

In another non-limiting embodiment, the plurality of staple drivers comprise first staple drivers and second staple drivers. The first staple drivers are configured to deploy at least one staple from the first, second, and third row of staples. For example, each first staple driver may be configured to deploy three staples from among the three rows of staples. Such staple drivers can be referred to as tri-staple drivers. The staples that are deployed may be longitudinally aligned or may be longitudinally offset. In one such embodiment, for example, the first staple driver may be configured to deploy a centrally-positioned staple of the second row of staples, a distally-positioned staple of the first row of staples, and a proximally-positioned staple of the third row of staples. The plurality of first staple drivers may be positioned proximal to the second staple drivers. As the firing member moves from a proximal starting position to a distal position, the actuation sled engages the plurality of first staple drivers to deploy the staples positioned in the first, second, and third rows of staples. The plurality of first staple drivers may be centrally-located between the proximal end of the staple cartridge body and the distal end of the staple cartridge body.

The first staple drivers positioned on one side of the longitudinal slot can be configured symmetrically with the first staple drivers positioned on the opposite side of the longitudinal slot. The symmetrical configuration and location within the staple cartridge body of the plurality of first staple drivers provide numerous benefits. First, as the firing member translates distally, the required amount of force to deploy the staples can increase. The location of the plurality of first staple drivers provides for uniform staple deployment as the firing member moves through the proximal and central portions of the staple cartridge. As the firing member approaches the distal end of the staple cartridge, the amount of force needed to deploy the staples can increase. The increased force needed to deploy the distal most staples can be addressed in numerous configurations as discussed in greater detail below. In addition, increasing hemostasis at the distal portion of the staple cartridge may be enhanced through different staple driver configurations, discussed in greater detail below.

In another non-limiting embodiment, for example, the second staple drivers may be configured to deploy a single staple. The second staple drivers may be positioned distally with respect to the plurality of first staple pushes. With each second staple driver deploying a singular staple, the amount of force needed to deploy each staple driver may be greatly reduced and may prevent the surgical instrument from causing unnecessary trauma to the distally most engaged tissue. In another embodiment, for example, the staple cartridge may comprise third staple drivers. Each third staple driver may be configured to deploy two staples from either the same row or different rows. Once again, the reduction in the number of staples being deployed by a single staple driver may reduce the amount of trauma that the tissue is exposed to. In one embodiment, the third staple driver may be positioned in the third row of staples to deploy two longitudinally spaced staples. The combination of second and third staple drivers disposed in the distal end of the staple cartridge body provides for an asymmetrical configuration that allows for better dispersion of the firing forces. The asymmetrical configuration of the second and third staple drivers, following the symmetrical configuration of the first staple drivers reduces the trauma the tissue is exposed to and may create desirable hemostasis effects.

In another embodiment, for example, the staple cartridge may comprise first staple drivers, second staple drivers, and third staple drivers. Each of the first, second, and third staple drivers may be configured to support and eject various combinations of staples such as, for example, one, two, three, four, five, or more staples. In certain embodiments, discussed in more detail below, the first, second, and third staple drivers can be arranged to provide advantageous staple deployment and to limit operation stress and fatigue to the staple cartridge and the tissue. For example, the first and second staple drivers can be aligned laterally-spaced, extending from the proximal most portion of the staple cartridge to the distal most portion of the staple cartridge. The third staple drivers may be located to at the distal end of the staple cartridge, the proximal end of the staple cartridge, or both. The advantageous of different staple driver configurations and the amount of staples each driver is configured to eject for the staple cartridge can provide numerous operation and healing benefits.

An example of a surgical stapler having linear rows of staples is disclosed in U.S. Pat. No. 6,669,073, entitled SURGICAL STAPLING APPARATUS, which issued on Dec. 30, 2003, the entire disclosure of which is incorporated herein by reference. As illustrated in FIG. 1 of the Subject Application, the surgical stapler is shown generally as 10. Surgical stapler 10 includes a trigger assembly 30, a body portion 12, a staple cartridge 40, and an anvil assembly 70. Trigger assembly 30 includes a pivotal trigger 32. Pivotal movement of trigger 32 during an actuation sequence of trigger 32 translates pivotal movement of trigger 32 into linear movement of a drive mechanism (not shown). The drive mechanism is operatively coupled to an actuation sled in staple cartridge 40 to translate linear movement of the drive mechanism to linear movement of the actuation sled. Stapler 10 is movable such that a portion of body tissue (not shown) may be positioned between anvil assembly 70 and staple cartridge 40. Actuation of stapler 10 moves anvil assembly 70 towards staple cartridge 40 thereby grasping or retaining the portion of body tissue therebetween. In addition, once the portion of body tissue is grasped between anvil assembly 70 and staple cartridge 40, continued actuation of stapler 10 discharges staples 50 (FIG. 2) through the portion of body tissue and against anvil assembly 70 to form completed staples 50. The presently disclosed staple drive assembly may be incorporated into staple cartridge 40 of surgical stapler 10 disclosed in U.S. Pat. No. 6,669,073, entitled SURGICAL STAPLING APPARATUS, which issued on Dec. 30, 2003. Alternately, a staple drive assembly may be incorporated into other known stapling devices including open-type surgical stapling devices, such as the open surgical staplers shown and described U.S. Pat. No. 4,955,959, entitled LOCKING MECHANISM FOR A SURGICAL FASTENING APPARATUS, which issued on Sep. 11, 1990; U.S. Pat. No. 4,978,049, entitled THREE STAPLE DRIVE MEMBER, which issued on Dec. 18, 1990; U.S. Pat. No. 5,395,034, entitled LINEAR SURGICAL STAPLING INSTRUMENT, which issued on Mar. 3, 1995; U.S. Pat. No. 5,630,541, entitled SURGICAL STAPLER AND STAPLE CARTRIDGE, which issued on May 20, 1997; U.S. Pat. No. 5,662,258, entitled SURGICAL STAPLER INSTRUMENT, which issued on Sep. 2, 1997; U.S. Pat. No. 6,131,789, entitled SURGICAL STAPLER, which issued on Oct. 17, 2000 and U.S. Pat. No. D278,081, entitled LINEAR ANASTOMOSIS SURGICAL STAPLE CARTRIDGE, which issued on Mar. 19, 1985. and other endoscopic or laparoscopic surgical stapling devices, such as the endoscopic staplers shown and described in U.S. Pat. No. 7,044,352, entitled SURGICAL STAPLING INSTRUMENT HAVING A SINGLE LOCKOUT MECHANISM FOR PREVENTION OF FIRING, which issued on May 16, 2006; U.S. Pat. No. 6,978,921, entitled SURGICAL STAPLING INSTRUMENT INCORPORATING AN E-BEAM FIRING MECHANISM, which issued on Dec. 27, 2005; and U.S. Pat. No. 7,143,923, entitled SURGICAL STAPLING INSTRUMENT HAVING A FIRING LOCKOUT FOR AN UNCLOSED ANVIL, which issued on Dec. 5, 2006, the entire disclosures of which are hereby incorporated by reference herein. While the present disclosure describes embodiments involving an actuation sled, it also will be appreciated that the design characteristics and function of the sled camming members may be incorporated directly into cam bars or firing wedges, which in turn are connected to the firing mechanism of the surgical stapling instrument.

Figure 2:
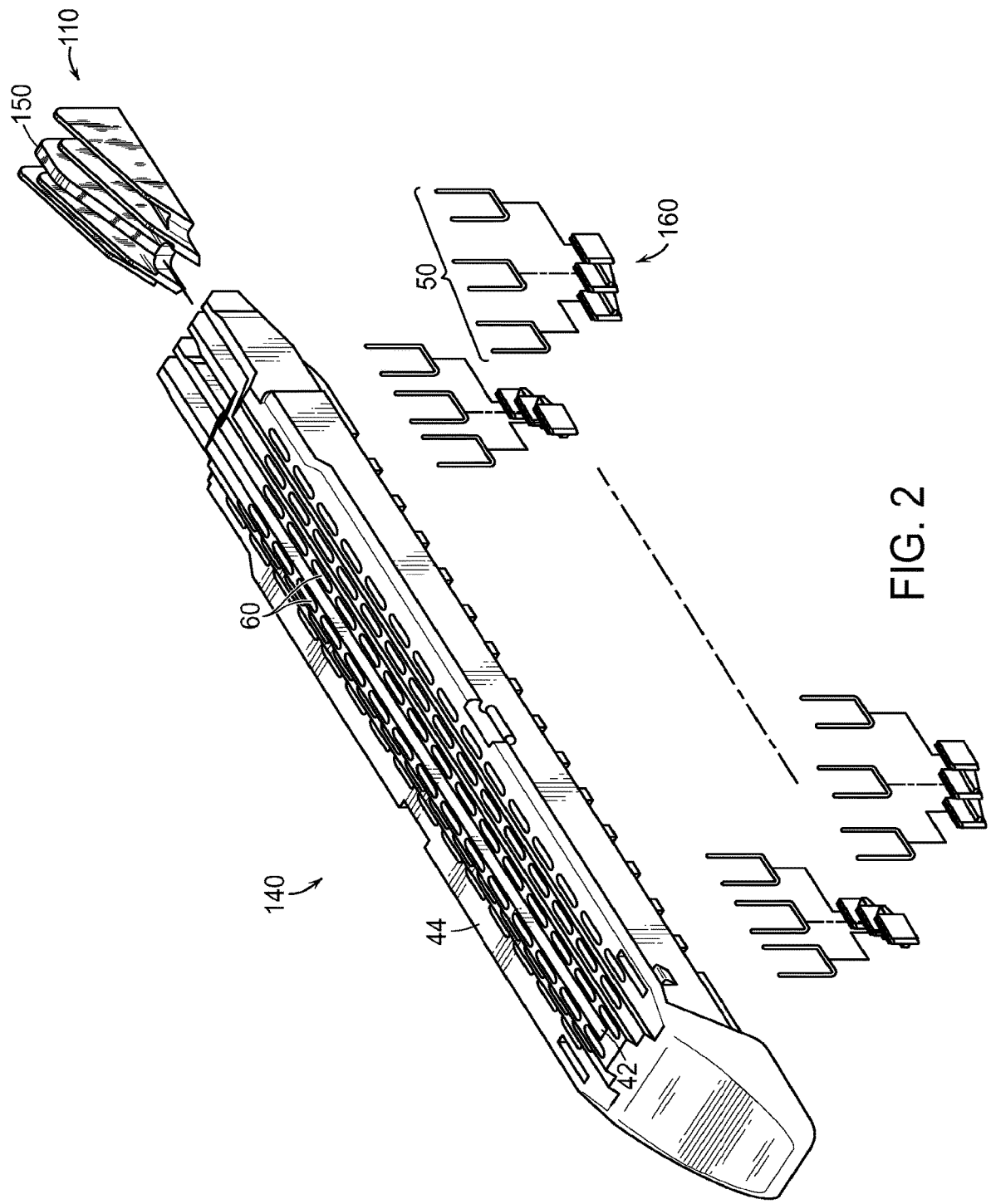
FIG. 2 is an exploded view of a staple cartridge assembly for use with the surgical instrument of FIG. 1.

FIG. 2 illustrates a staple cartridge 140 including a staple drive assembly. Staple cartridge 140 includes a plurality of fasteners or staples 50 and a corresponding number of staple pockets or retention slots 60. A tissue contacting surface 44 is defined by a top surface of staple cartridge 140. A guide channel 42 extends substantially the length of staple cartridge 140 and is adapted for slidably receiving guide member 150 of actuation sled 110. Guide channel 42 cooperates with guide member 150 for aligning and positioning actuation sled 110 in staple cartridge 140 as it translates longitudinally from a proximal end to a distal end of staple cartridge 140. As actuation sled 110 translates distally from the proximal end to the distal end of staple cartridge 140, the actuation sled 110 sequentially engages staple drivers 160 to eject staples 50 from the staple cartridge 140. Guide channel 42 may also facilitate passage of a knife blade (not shown) through cartridge 140, such as by mounting a knife blade to guide member 150.

FIG. 3 illustrates a staple cartridge 240 including a tissue contacting surface 244. A guide channel 242 extends substantially the length of staple cartridge 240 and is adapted for slidably receiving guide member 150 of actuation sled 110. As seen in FIG. 3, tissue contacting surface 244 includes first, second, and third tissue contacting surfaces 230, 232, and 234 on one side of the guide channel 242. Specifically, tissue contacting surfaces 230, 232, and 234 are planar structures that are substantially parallel to one another, but are not co-planar with one another (i.e. the tissue contacting portion is stepped). Staple cartridge 240 further comprises a plurality of staple cavities 260. The first tissue contacting surface 230 comprises a first row of staple cavities 231. The second tissue contacting surface 232 comprises a second row of staple cavities 233. The third tissue contacting surface 234 comprises a third row of staple cavities 235. The staple cartridge 240 also comprises an additional first tissue contacting surface 230, a first row of staple cavities 231, a second tissue contacting surface 232, a second row of staple cavities 233, a third tissue contacting surface 234, and a third row of staple cavities 235 on the opposite side of the guide channel 242. Moreover, although the drawings show planar tissue contacting surfaces 230, 232, and 234, the present disclosure envisions curved and/or angled tissue contacting surfaces as well as other kinds of tissue contacting surfaces having other shapes and structures.

FIG. 4 illustrates different configurations of staple drivers for use within staple cartridges 40, 140, and/or 240, for example. Staple driver 360 is configured to support a single staple (not shown) and comprises staple retaining feature 361. Staple driver 362 is configured to support two staples (not shown) and comprises two staple retaining features 363. Staple driver 364 is configured to support three staples (not shown) and comprises three staple supporting features 365. Such staple drivers can be referred to as tri-staple drivers. Staple supporting features 361, 363, and 365 are configured to support the staples positioned thereon and limit relative movement between the staples and the staple supporting features in one or more directions. The different variations and combinations of staple drivers within staple cartridge 40, 140, 240, will be discussed in further detail in the following embodiments. Additional combinations and configurations of staple drivers are within the scope of the present disclosure.

Figure 5:
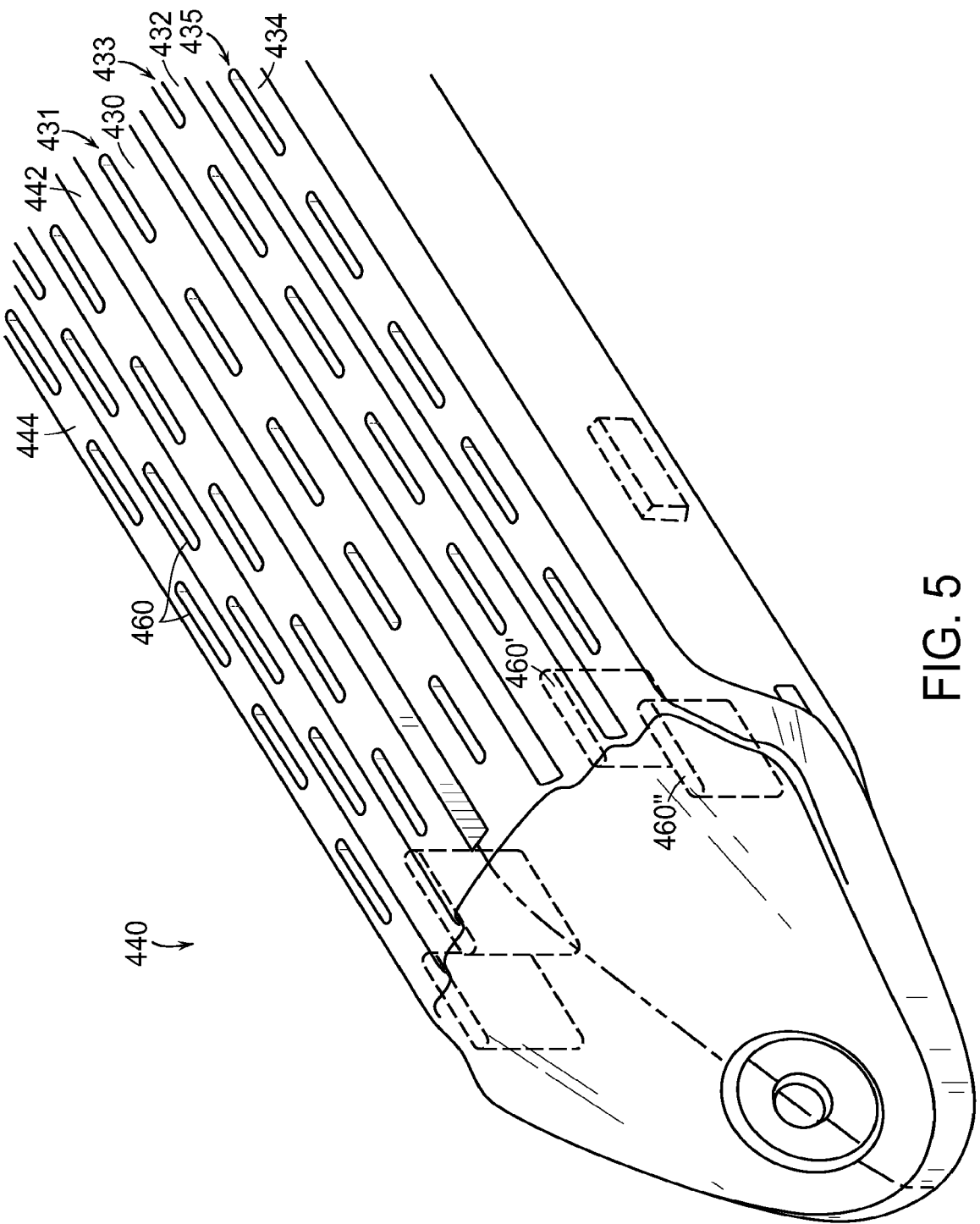
FIG. 5 is a partial perspective view of a staple cartridge assembly.

FIG. 5 illustrates a staple cartridge 440 including a plurality of staple cavities 460. A guide channel 442 extends substantially the length of staple cartridge 440 and is adapted for slidably receiving guide member 150 of actuation sled 110. As seen in FIG. 5, tissue contacting surface 444 includes first, second, and third tissue contacting surfaces 430, 432, and 434 on one side of the guide channel 442. Specifically, tissue contacting surfaces 430, 432, and 434 are planar structures that are substantially parallel to one another, but are not co-planar with one another (i.e. the tissue contacting portion is stepped). Staple cartridge 440 further comprises a plurality of staple cavities 460. Each of the first, second, and third tissue contacting surfaces are positioned in different planes. The first tissue contacting surface 430 comprises a first row of staple cavities 431. The second tissue contacting surface 432 comprises a second row of staple cavities 433. The third tissue contacting surface 434 comprises a third row of staple cavities 435. The first, second, and third row of staple cavities extend between a proximal end and a distal end of the staple cartridge 440. The staple cartridge 440 also comprises an additional first tissue contacting surface 430, a first row of staple cavities 431, a second tissue contacting surface 432, a second row of staple cavities 433, a third tissue contacting surface 434, and a third row of staple cavities 435 on the opposite side of the guide channel 442. Although the drawings show planar tissue contacting surfaces 430, 432, and 434, the present disclosure envisions curved or angled tissue contacting surfaces as well as other kinds of tissue contacting surfaces having other shapes and structures.

The distal-most staple cavity of the second row of staple cavities 433, further to the above, comprises an empty staple cavity 460' comprising an empty staple driver, wherein the staple retaining feature of the empty staple cavity 460' does not support and/or retain a staple. The distal-most staple cavity of the third row of staple cavities 435 comprises an empty staple cavity 460" comprising an empty staple driver, wherein the staple retaining feature of the empty staple cavity 460" does not support and/or retain a staple. Notably, the staple cavities 460' and 460" are empty prior the staple cartridge 440 being fired, or at least partially fired, during a firing cycle. In such instances, the proximal staple cavities 460 include a staple removably stored therein while the distal staple cavities 460' and 460" do not include a staple removably stored therein.

The distal-most staple drivers of staple cartridge 440 may be configured similar to the staple drivers illustrated in FIG. 4 and described above. For instance, a staple driver can comprise one staple retaining feature, two staple retaining features, or three or more staple retaining features, for example. In the instances where the distal-most staple driver comprises three or more staple retaining features, for example, the distal-most staple driver may be partially loaded such that not all of the staple retaining features support a staple prior to the firing cycle. It is envisioned that an empty staple retaining feature may be modified or replaced, for example, to be flat and/or remain below the tissue contacting surface 444. Alternatively, an empty staple retaining feature may comprise a tissue engaging feature which engages the tissue when the staple driver is lifted upwardly.

Figure 6:
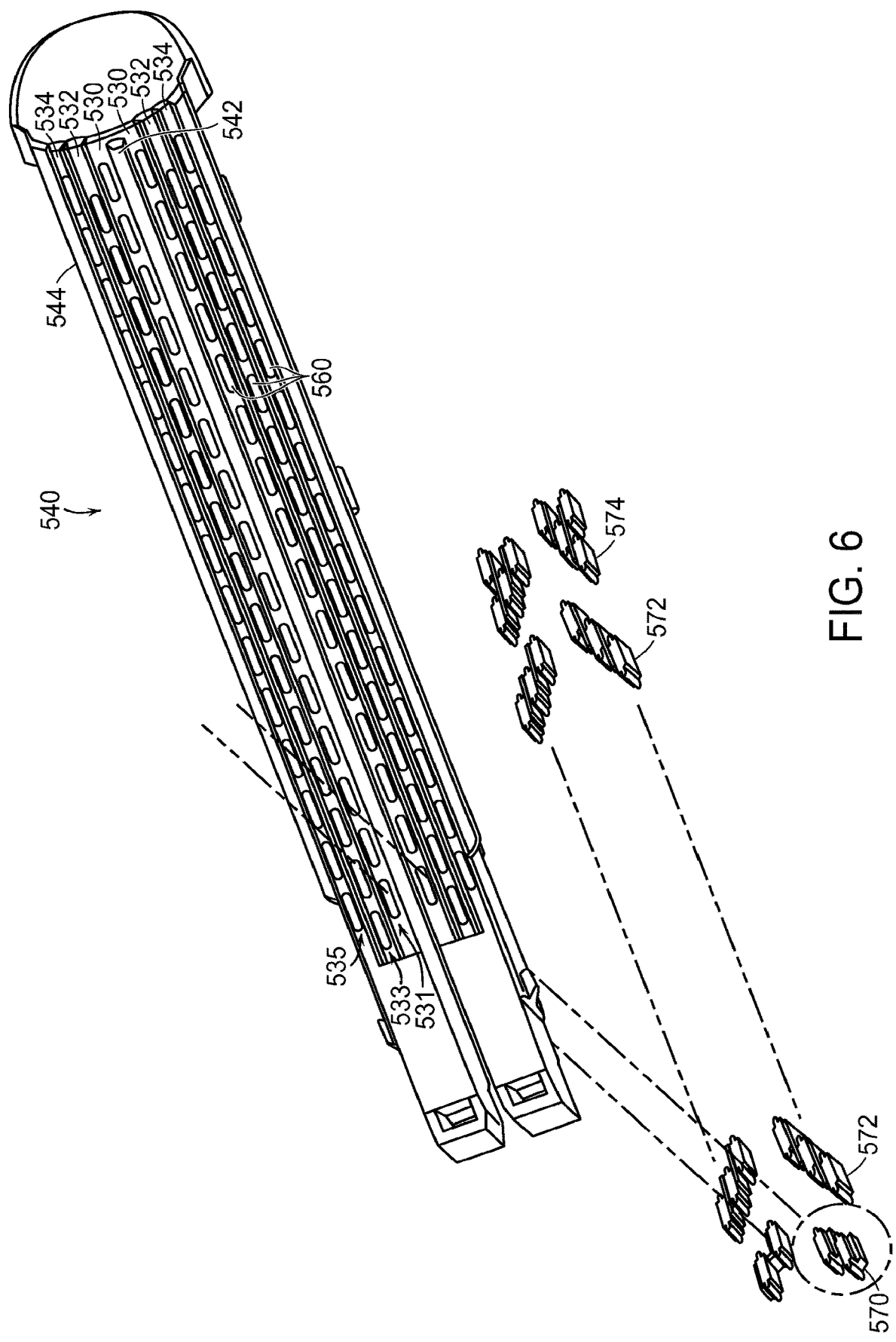
FIG. 6 is an exploded perspective view of a surgical staple cartridge assembly illustrated with some components removed for the purposes of illustration.

Referring now to FIG. 6, a staple cartridge 540 includes a tissue contacting portion 544. Tissue contacting portion 544 includes first, second, and third tissue contacting surfaces 530, 532, and 534. Specifically, tissue contacting surfaces 530, 532, and 534 are planar structures that are substantially parallel to one another, but are not co-planar with one another (i.e. the tissue contacting portion is stepped). A set of tissue contacting surfaces 530, 532, 534 is disposed on each side of knife channel 542. The first tissue contacting surfaces 530 have a knife channel 542 defined therein. The tissue contacting surfaces 530 are co-planar with one other. The second tissue contacting surfaces 532 are co-planar with one another. The third tissue contacting surfaces 534 are co-planar with one another. The first, second, and third tissue contacting surfaces 530, 532, and 534 have different heights as measured from knife channel 542. Although the drawings show planar tissue contacting surfaces 530, 532, and 534, the present disclosure envisions curved or angled tissue contacting surfaces as well as other kinds of tissue contacting surfaces having other shapes and structures.

A wall or any other suitable structure interconnects first and second tissue contacting surfaces 530 and 532. Similarly, a suitable structure such as a wall interconnects second and third contacting surfaces 532 and 534. The walls or interconnecting structures may be oriented orthogonally with respect to the tissue contacting surfaces 530, 532, 534. The present disclosure, however, contemplates walls or interconnecting structures oriented in different directions such as angled, curved or other configurations.

In at least one embodiment, first tissue contacting surface 530 has the greatest height, third tissue contacting surface 534 has the least height, and second tissue contacting surface 532 has a height between the heights of first and third tissue contacting surfaces 530, 534. While tissue contacting surfaces 530, 532, 534 are shown as decreasing in height from first tissue contacting surface 530 to third tissue contacting surface 543, it is envisioned that the heights of each tissue contacting surface may vary depending on the particular surgical procedure. Other features of tissue contacting surfaces 530, 532, 534 may also vary according to the circumstances.

Each tissue contacting surface 530, 532, 534 includes a plurality of staple cavities 560 formed therein. Staple cavities 560 are disposed in a first, second, and third row of staple cavities 531, 533, 535 that are located in tissue contacting surfaces 530, 532, 534 respectively. The linear rows of staple cavities 531, 533, 535 are staggered along the longitudinal axis of staple cartridge 540 as shown in FIG. 6. Particularly, the distal most staple cavities 560 of the first and third rows of staple cavities 531, 535 are closer to the distal end of cartridge 540 than the distal most staple cavity 560 of the second row of staple cavities 533. On the other hand, the most proximal staple cavity 560 of the second row of staple cavities 533 is closer to the proximal end of cartridge 540 than the most proximal staple cavity 560 of the first and third row of staple cavities 531, 535. Linear rows of staple cavities 531, 533, 535 having other suitable arrangements are within the scope of the present disclosure.

FIG. 6 further depicts staple cartridge 540 comprising a plurality of staple drivers. While many different configurations of staple drivers are within the scope of the present disclosure, FIG. 6 discloses one such configuration. Proximal staple drivers 570 may be configured to support one or more staples, such as two staples, prior to the firing cycle. Proximal staple drivers 570 are positioned in the proximal-most staple cavities 560 of the staple cartridge 540. Distal staple drivers 574 may be configured to support one or more staples, such as four staples, prior to the firing cycle. Distal staple drivers 574 are positioned in the distal-most staple cavities 560 of the staple cartridge 540. Central staple drivers 572 may be configured to support one or more staples, such as three staples, prior to the firing cycle. When central staple drivers 572 are configured to support three staples, they can be referred to as tri-staple drivers. Central staple drivers 572 are positioned in the central staple cavities 560 between the proximal staple drivers 570 and the distal staple drivers 574. FIG. 6 depicts proximal staple drivers 570 that are configured to support two staples, central staple drivers 572 configured to support three staples, and distal staple drivers 574 configured to support four staples prior to the firing cycle; however, other configurations are within the scope of the present disclosure. It is also within the scope of the present disclosure for a staple driver to support less than the total amount of staples that the staple driver is configured to support.

Figure 7:
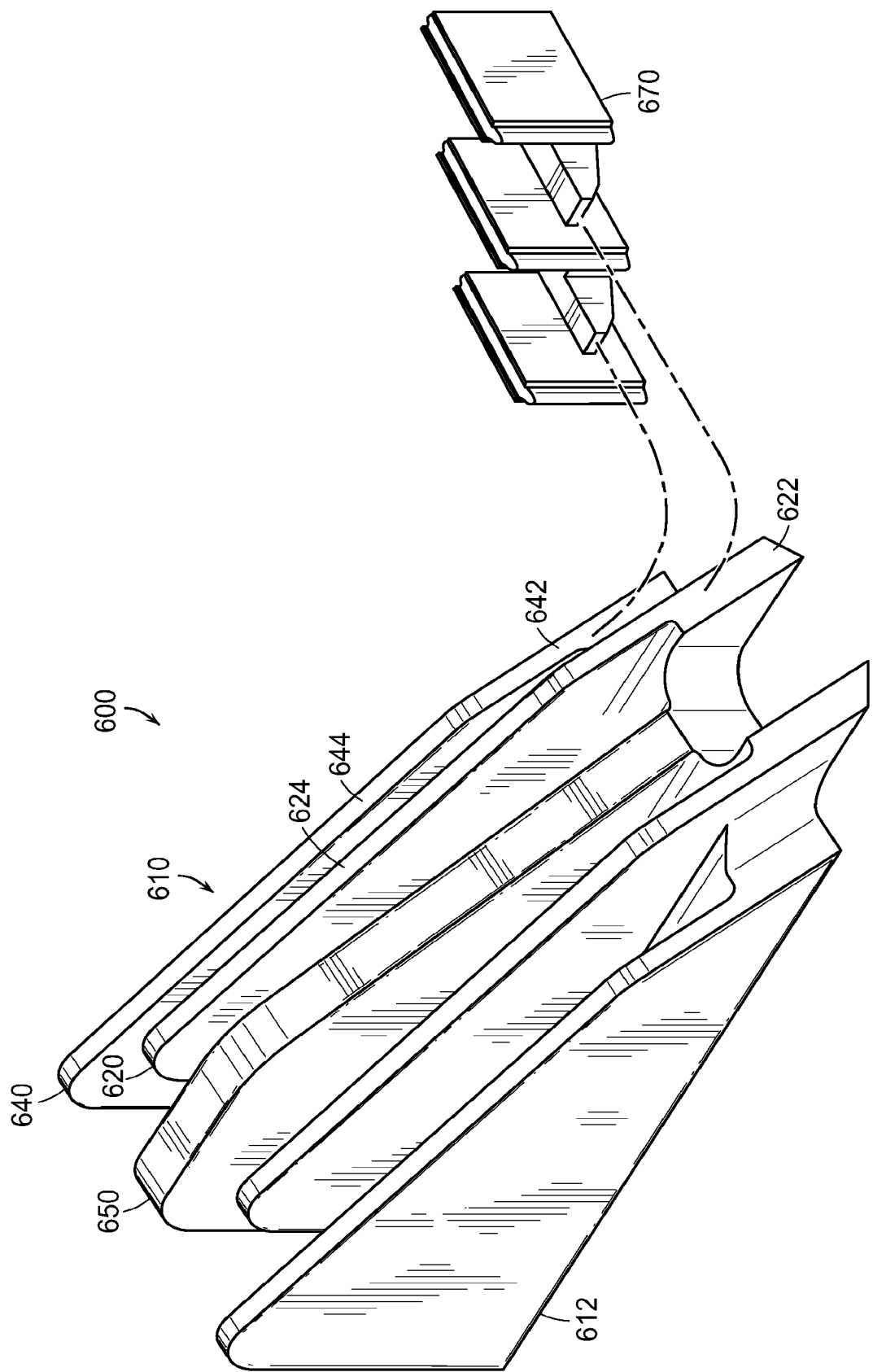
FIG. 7 is a perspective view of an actuation sled and a staple driver.

FIG. 7 depicts a staple drive assembly 600. Staple drive assembly 600 includes an actuation sled 610 and at least one staple driver 670. Actuation sled 610 includes a base 612, a first camming member 620, a second camming member 640, and a guide member 650. First and second camming members 620, 640 include respective first or leading cam wedges 622, 642 and respective second or trailing cam wedges 624, 644. In at least one embodiment, staple drive assembly 600 is adapted for use in a surgical stapler, such as an endoscopic or laparoscopic stapler, for example, having at least two linear rows of staples. As seen in FIG. 7, the first camming member 620 extends further distally than the second camming member 640, which, in some staple driver configurations, permits the inner most staple drivers to be ejected before and/or ahead of the outermost staples. The actuator sled 610 depicted in FIG. 7 is configured to lift staple drivers 670 on a first side thereof and staple drivers having a mirror image to that of staple drivers 670 on a second, or opposite, side thereof wherein each of the staple drivers can each be configured to support three staples thereon; however, the actuator sled 610 is configured to lift any suitable arrangement of staple drivers and staples. When the staple drivers 670 are configured to support three staples, they can be referred to as tri-staple drivers.

Figure 8:
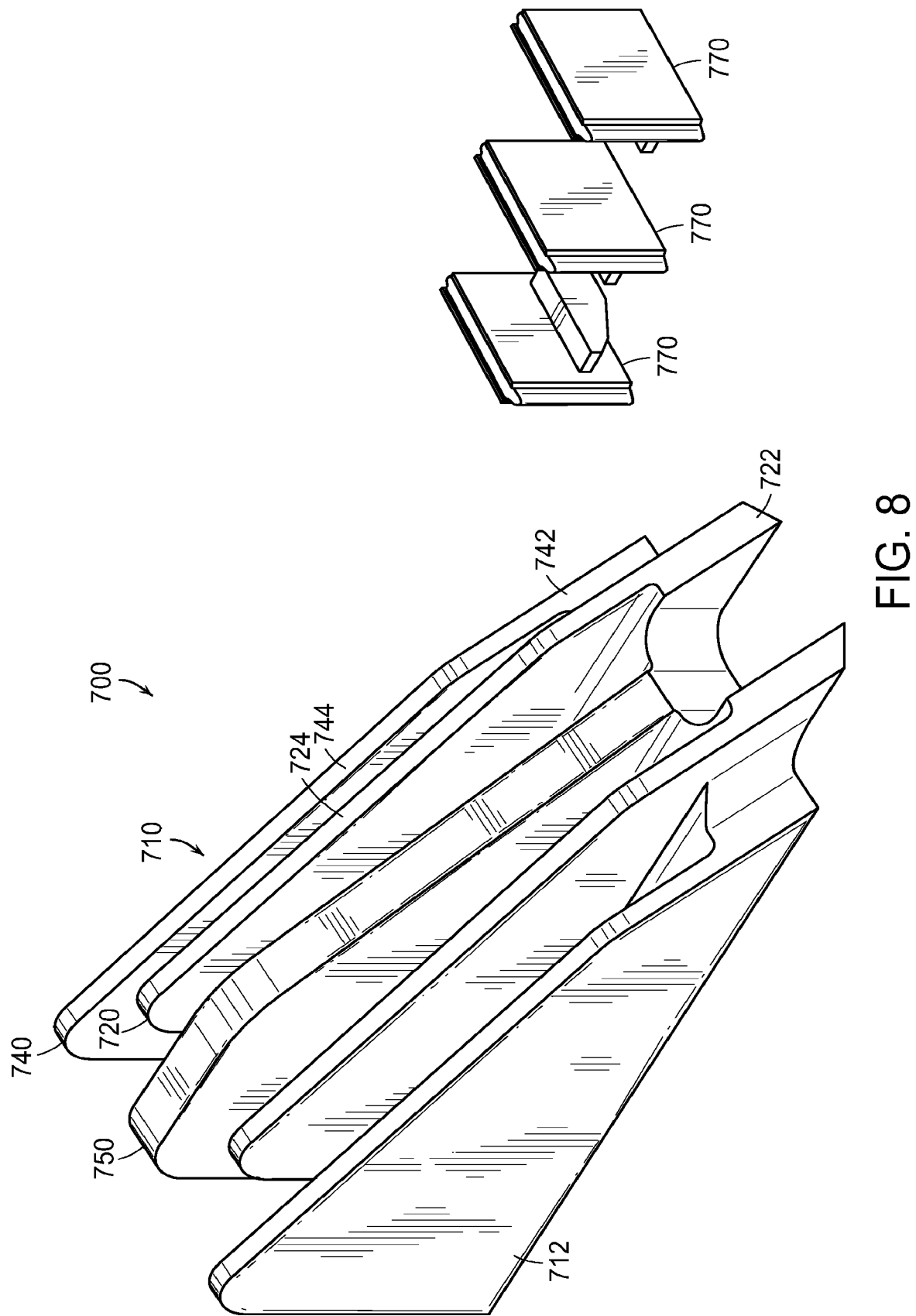
FIG. 8 is a perspective view of an actuation sled and a staple driver.

FIG. 8 depicts a staple drive assembly 700. Staple drive assembly 700 includes an actuation sled 710 and a plurality of staple drivers 770. Actuation sled 710 includes a base 712, a first camming member 720, a second camming member 740, and a guide member 750. First and second camming members 720, 740 include respective first or leading cam wedges 722, 742 and respective second or trailing cam wedges 724, 744. In at least one embodiment, staple drive assembly 700 is adapted for use in a surgical stapler, such as an endoscopic or laparoscopic stapler, for example, having at least two linear rows of staples. As seen in FIG. 8, the first camming member 720 extends further distally than the second camming member 740, which, in some staple driver configurations, permits the inner most staple drivers to be ejected before and/or ahead of the outermost staples. The actuator sled 710 depicted in FIG. 8 is configured to lift staple drivers 770 on a first side thereof and staple drivers having a mirror image to that of staple drivers 770 on a second, or opposite, side thereof wherein each of the staple drivers can each be configured to support one staple thereon; however, the actuator sled 710 is configured to lift any suitable arrangement of staple drivers and staples.

Figure 9:
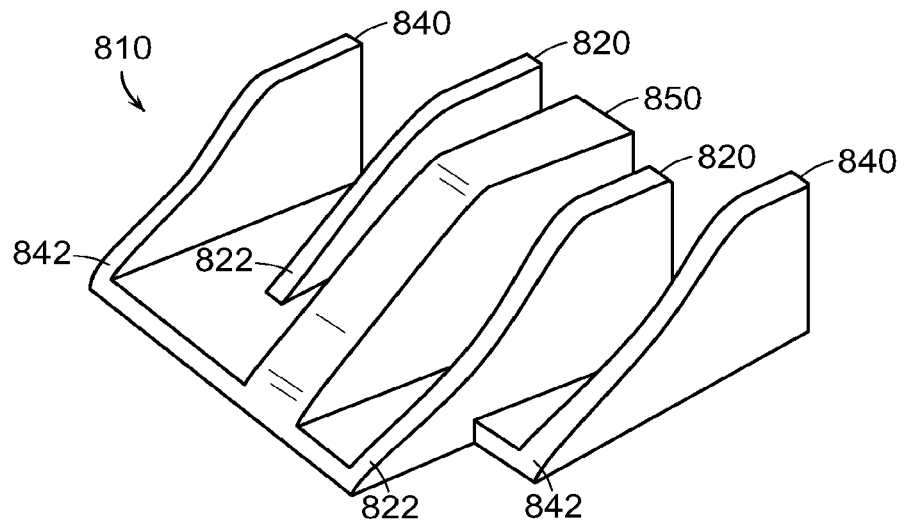
FIG. 9 is a perspective view of an actuation sled.

FIG. 9 depicts actuation sled 810 comprising first camming members 820, second camming members 840, and a guide member 850. The actuation sled 810 comprises a first camming member 820 and a second camming member 840 on a first side of the guide member 850 and a first camming member 820 and a second camming member 840 on a second side of the guide member 850. Each first camming member 820 comprises a first or leading cam wedge 822 and each second camming member 840 comprises a second or leading cam wedge 842. The first camming members 820 of the actuation sled 810 are offset longitudinally from one another. The second camming members 840 are also offset longitudinally from one another. The offset configuration of the first and second camming members 820, 840 permits the staple drivers to be fired in a particular configuration for desired hemostasis effects.

Figure 10:
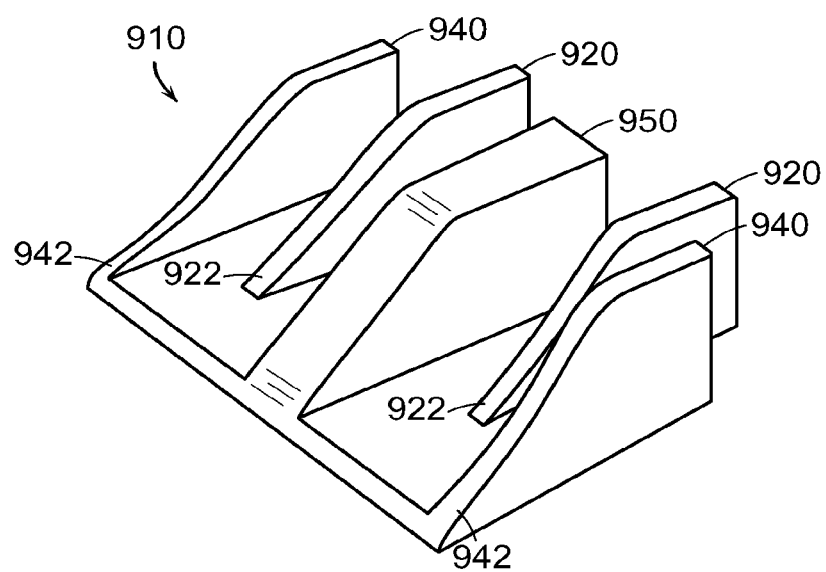
FIG. 10 is a perspective view of an actuation sled.

FIG. 10 depicts actuation sled 910 comprising first camming members 920, second camming members 940, and a guide member 950. The actuation sled 910 comprises a first camming member 920 and a second camming member 940 on a first side of the guide member 950 and a first camming member 920 and a second camming member 940 on a second side of the guide member 950. Each first camming member 920 comprises a first or leading cam wedge 922 and each second camming member 940 comprises a second or leading cam wedge 942. The first camming members 920 of the actuation sled 910 are aligned longitudinally with one another. The second camming members 940 are also aligned longitudinally with one another. The aligned configuration of the first and second camming members 920, 940 permits the staple drivers to be fired in a particular configuration for desired hemostasis effects.

Figure 11:
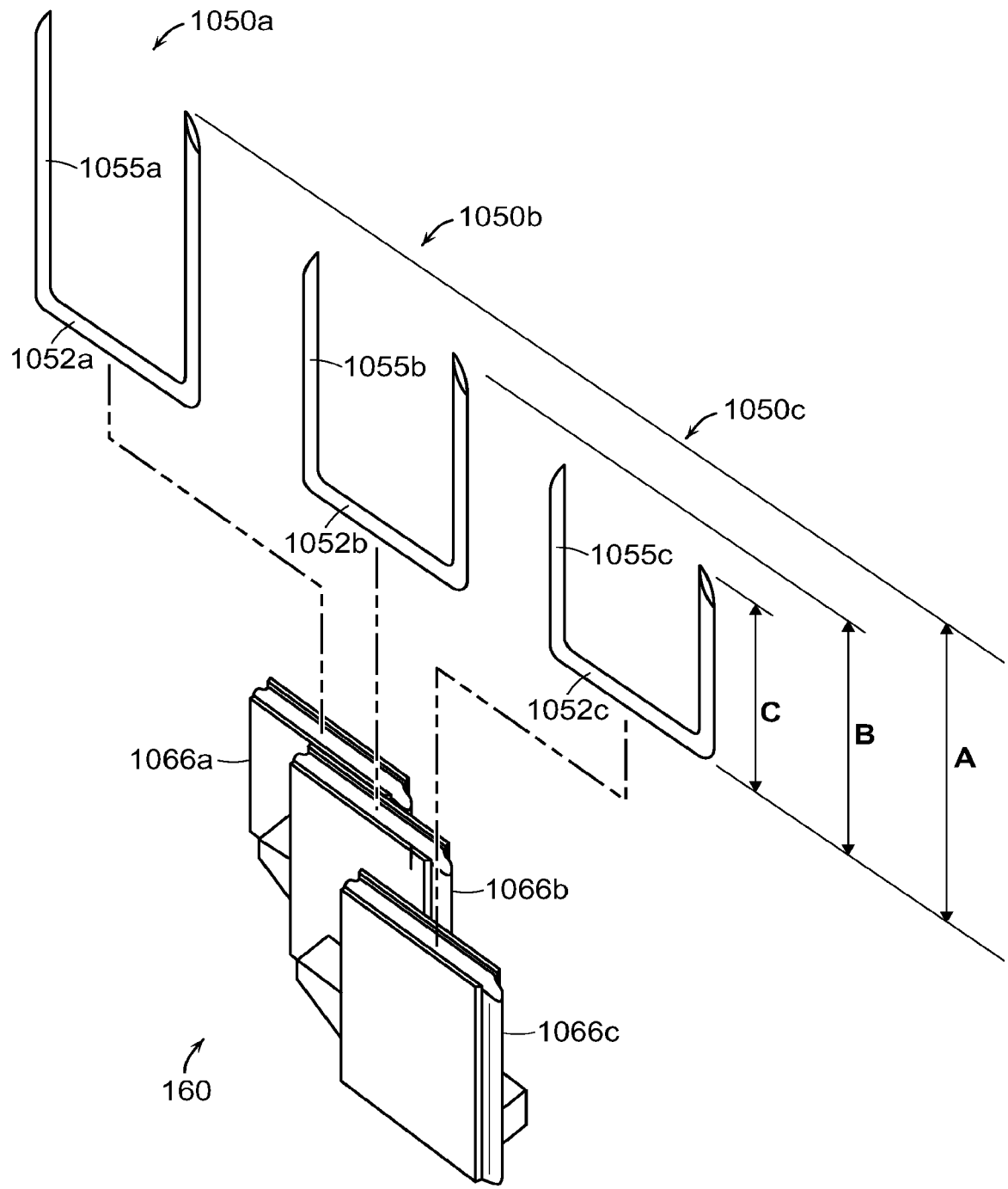
FIG. 11 illustrates a staple driver and staples which are supported by the staple driver.

FIG. 11 illustrates an arrangement of the staples 1050*a*, 1050*b*, and 1050*c* in the staple cartridge 140 (FIG. 2). Each staple 1050*a* comprises a backspan 1052*a*, each staple 1050*b* comprises a backspan 1052*b*, and each staple 1050*c* comprises a backspan 1052*c*. Legs 1055*a* of surgical fasteners 1050*a* have a first leg length "A", legs 1055*b* of surgical fasteners 1050*b* have a second leg length "B", and legs 1055*c* of surgical fasteners 1050*c* have a third leg length "C." In one embodiment, first length "A" is greater than second length "B." In turn, second length "B" is greater than third length "C." U.S. Patent Application Publication No. 2007/0131732 describes an embodiment of the disclosed fastener arrangement. The entire disclosure of U.S. Patent Application Publication No. 2007/0131732, entitled SURGICAL STAPLING INSTRUMENTS INCLUDING A CARTRIDGE HAVING MULTIPLE STAPLE SIZES, which was filed on Nov. 3, 2006, is incorporated by reference herein. The present disclosure, however, contemplates other fastener arrangements. Surgical fasteners 1050*a-c* are configured to operate in conjunction with staple driver 160, for example, which is described above.

The longitudinal translation of sled 110 through staple cartridge 140 urges staple drivers 160 in a vertical direction to eject staples 1050*a-c* during a firing cycle. As shown in FIG. 11, staple driver 160 includes staple pushers 1066*a-c*, each of which has a different vertical dimension. Staple pusher 1066*c* has the greatest vertical dimension and cooperates with staple 1050*c*, which has the smallest leg length. Staple pusher 1066*a* has the smallest vertical dimension and cooperates with staple 1050*a*, which has the largest leg length. Staple pusher 1066*b* has a vertical dimension greater than staple pusher 1066*a*, but less than staple pusher 1066*c* and cooperates with staple 1050*b*, which has an intermediate leg length, i.e., a length between those of staples 1050*a* and 1050*c*. The staples 1050*c* are arranged adjacent knife channel 42, the staples 1050*a* are adjacent the outer edge of cartridge 140, and the staples 1050*b* are disposed therebetween. By providing staples 1050*a-c* and staple pushers 1066*a-c* with complementary heights, the various sized-staples are formed against the anvil of the stapler into the desired shape. It is also envisioned that other arrangements of driver pushers and surgical fasteners may be used.

Staples having different leg lengths may be arranged so that the staples with the larger leg lengths are arranged adjacent the knife channel 42. In addition, the staple cartridge 140 may have a single planar tissue contacting surface and the anvil member may be provided with more than one tissue contacting surface so as to define more than one gap with respect to the tissue contacting surface of the staple cartridge. One or both of the staple cartridge and anvil member may have stepped surfaces, angled or sloped surfaces, or curved surfaces that are selected to correspond to staples having predetermined leg lengths. In certain embodiments, more than one tissue contacting surface is provided, on the staple cartridge, the anvil member, or both, with sloped surfaces extending therebetween. In certain embodiments, the staple pushers have heights corresponding to the different staple sizes. The anvil pockets of the anvil assembly, the staple drivers, and/or the actuation sled are arranged to form each of the different sized staples in the desired closed shapes.

Figure 12:
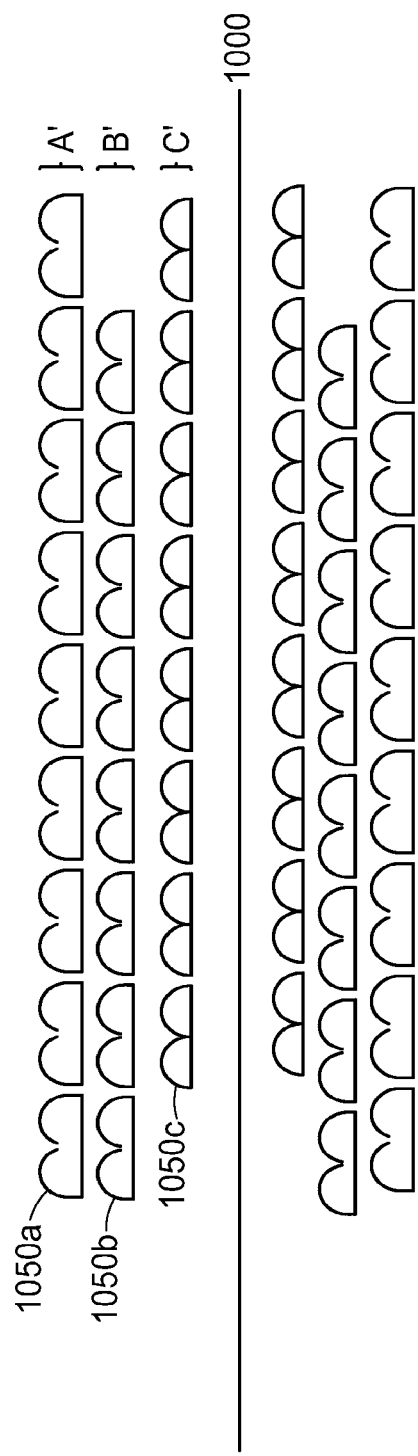
FIG. 12 illustrates formed staple lines having different formed heights.

FIG. 12 illustrates three rows of staples formed on each side of a cut line 1000 utilizing formed to a first formed staple height A', a second formed staple height B', and a third formed staple height C'. Formed height A' corresponds to staples 1050*a* having a first unformed height A. Staples 1050*a* have the largest unformed and formed heights A and A', respectively. Formed height B' corresponds to staples 1050*b* having a second unformed height B. Staples 1050*b* have the second largest unformed and formed heights B and B', respectively. Formed height C' corresponds to staples 1050*c* having an unformed height C. Staples 1050*c* have the smallest unformed and formed heights C and C', respectively. While FIG. 12 depicts once such configuration of formed and unformed staple heights, different staple heights are within the scope of the present disclosure. For example, each staple 1050*a-c* could have the same formed heights and the same unformed heights, the same unformed heights but different formed heights, the same formed heights but different unformed heights, or any other possible combination.

FIGS. 13-24 depict numerous embodiments comprising various staple driver configurations. Each configuration provides certain characteristics and benefits. FIG. 13 depicts a staple cartridge 1140 having a stepped deck, a plurality of staple cavities 1160 defined in the deck, a proximal end P, and a distal end D. Staple cartridge 1140 further comprises proximal staple drivers 1170 configured to support two staples and distal staple drivers 1174 configured to support three staples. Distal staple drivers 1174 can be referred to as tri-staple drivers. The staple drivers 1170 and 1174 are both configured to eject a staple in the outer-most row, i.e., the row furthest away from the knife channel 1142, and, in addition, a staple in the intermediate row, i.e., the row adjacent the outer-most row. The staple drivers 1174 are also configured to eject a staple in the inner-most row, i.e., the row adjacent the knife channel 1142. The staple drivers 1170 and 1174 form an inside-out staple pattern. This pattern results in an isolated distal staple cavity 1160'. The isolated staple cavity 1160' can be empty, i.e., it may not include a staple positioned therein. Alternatively, the isolated staple cavity 1160' can include a staple positioned therein which is ejected by a driver having a single staple support plate. One characteristic of the embodiment of FIG. 13 is that it provides for the longitudinally-leading staple supported by each distal staple driver 1174, which is positioned in the outer row, to be formed before the laterally-adjacent staple in the inner row. With the cooperation of the distal staple drivers 1174 on both sides of the knife channel 1142, the distal staple drivers 1174 can form a "V" shaped configuration. This V-shaped configuration can push fluid within the tissue that is being stapled inwardly toward the cut line 1000 and distally toward the distal end of the cartridge 1140. This configuration provides for a central concentration of the fluid.

In the instances where the distal staple cavity 1160' of the staple cartridge is empty, the empty distal staple cavity 1160' can reduce the possibility of double-stapling a particular region of tissue. More particularly, it is quite frequent that several staple cartridges are utilized during a surgical procedure to form staple lines which are arranged in an end-to-end manner and the absence of a staple at the distal end of each staple line may reduce the possibility of a staple at the distal end of a staple line becoming overlapped with a staple at the proximal end of an adjacent staple line. When staples are overlapped with one another, the force required to fire the staples may increase significantly, especially at the beginning and/or end of a firing stroke. Although not illustrated in FIG. 13, a staple cartridge can include an empty proximal staple cavity to achieve the benefits described above.

FIG. 14 depicts a staple cartridge 1240 having a stepped deck, a proximal end P, a distal end D, and a knife slot 1242. Staple cartridge 1240 further comprises single staple drivers 1270 configured to support one staple and double staple drivers 1274 configured to support two staples. The staple drivers 1270, 1274 are arranged in an alternating configuration which permits three staples to be formed concurrently on each side of the knife slot 1242 in a staggered, but balanced, manner. The double staple driver 1274 provides stability in ejecting the staples as each double staple driver 1274 has two staple pusher plates which are aligned laterally. This configuration reduces the amount of firing force needed to fire the staple drivers. Moreover, as the staples are fired in an alternating pattern, a smaller area of tissue is affected with the firing of each staple driver.

Figure 15:
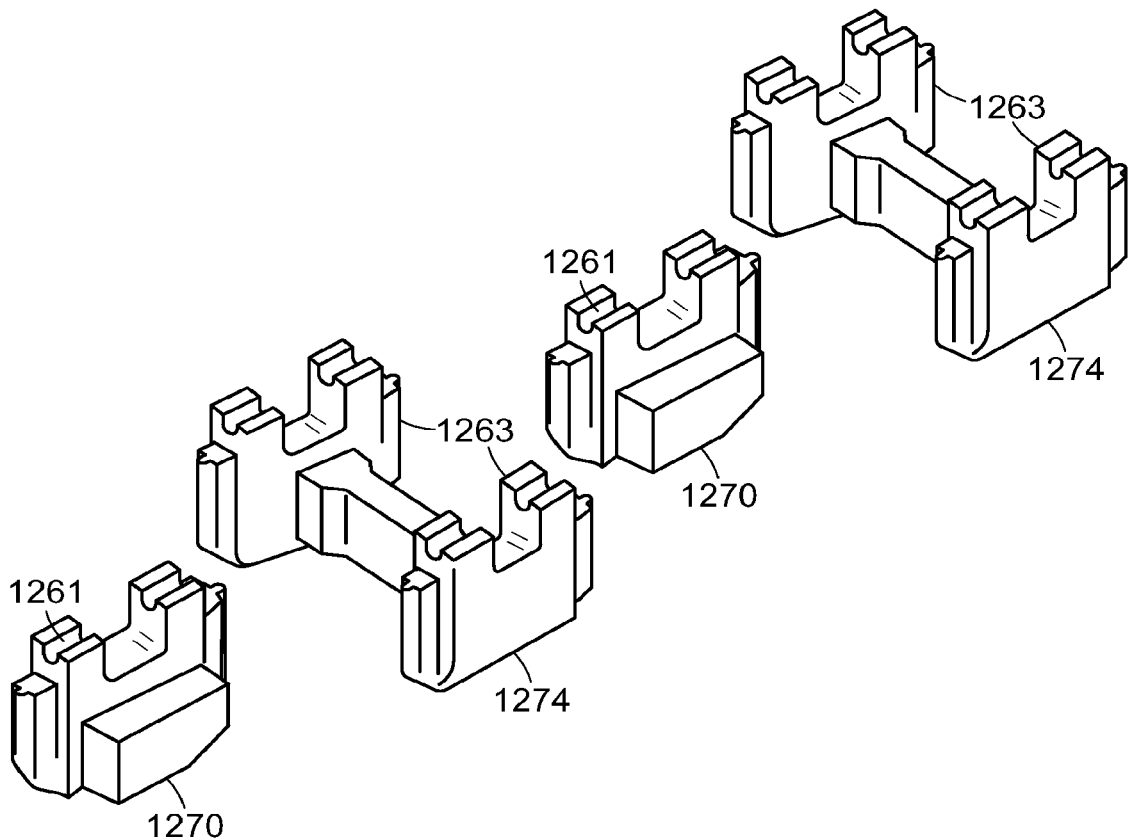
FIG. 15 is a perspective view of the staple driver arrangement of FIG. 14.

FIG. 15 depicts the staple drivers 1270, 1274 as shown in FIG. 14. As seen in FIG. 15, each single staple driver 1270 comprises one staple supporting feature 1261 and supports a single staple in the middle, or intermediate, staple row. Each double staple driver 1274 comprises two staple supporting features 1263 and supports a staple in the inner staple row and a staple in the outer staple row. The staple supporting features 1263 of each staple driver 1274 are connected by a bridge which extends across the row of intermediate drivers 1270. As a result of the above, the staple supporting features 1263 of the double staple drivers 1274 straddle the staple forming features 1261 of the staple drivers 1270. In various instances, further to the above, one of the staple supporting features 1263 of the double staple drivers 1270 may not include a staple positioned thereon in order to achieve strategic hemostasis effects under specific conditions.

FIG. 16 depicts a staple cartridge 1340 having a stepped deck, a proximal end P, and a distal end D. Staple cartridge 1340 further comprises proximal staple drivers 1370 configured to support two staples, central staple drivers 1372 configured to support three staple and distal staple drivers 1374 comprising three staple supporting features. Unlike each central staple driver 1372 which is intended to support three staples on its three staple supporting features, each distal staple driver 1374 is intended to support only one staple in use. This staple driver configuration provides for the completion of a uniform and secure staple line without the need for a distal staple driver configuration which is different than the preceding driver configurations. Moreover, this staple driver configuration is similar to the one disclosed in FIG. 13 and comprises the same benefits of the "V" shape formation as discussed above. Staple drivers 1372 and 1374 can be referred to as tri-staple drivers.

As discussed above, the distal staple drivers 1374 are only partially loaded. In certain instances, the distal staple drivers 1374, when actuated, can remain below the deck of the staple cartridge 1340. In other instances, the distal drivers 1374 can be pushed partially above the deck of the staple cartridge 1340, or overdriven, when actuated. In at least one such instance, the distal drivers 1374 can be configured to engage, grip, and/or hold the tissue positioned above the staple cartridge 1340.

FIG. 17 depicts a staple cartridge 1440 having a stepped deck configured as discussed in previous embodiments. The staple cartridge 1440 comprises a proximal end P and a distal end D. Staple cartridge 1440 comprises proximal staple drivers 1470 which support two staples, central staple drivers 1472 which support three staples and distal staple drivers 1474 which support one staple. Central staple drivers 1472 can be referred to as tri-staple drivers. The configuration of the distal staple drivers 1474 provides for the completion of a uniform and secure staple line. The single staple driver at the distal end of the firing stroke reduces the amount of force needed to fire the distal most staple, where the forces applied to the tissue may be the greatest. Furthermore, in the event that the actuation sled fails to complete the firing cycle, it is advantageous to limit the number of incompletely fired staples by reducing the number of potentially incompletely fired staples by reducing the capacity of the distal staple drivers 1474. Furthermore, the staple driver configuration is similar to the one disclosed in FIG. 13 and comprises the same benefits of the "V" shape formation line as discussed above.

Figure 18:
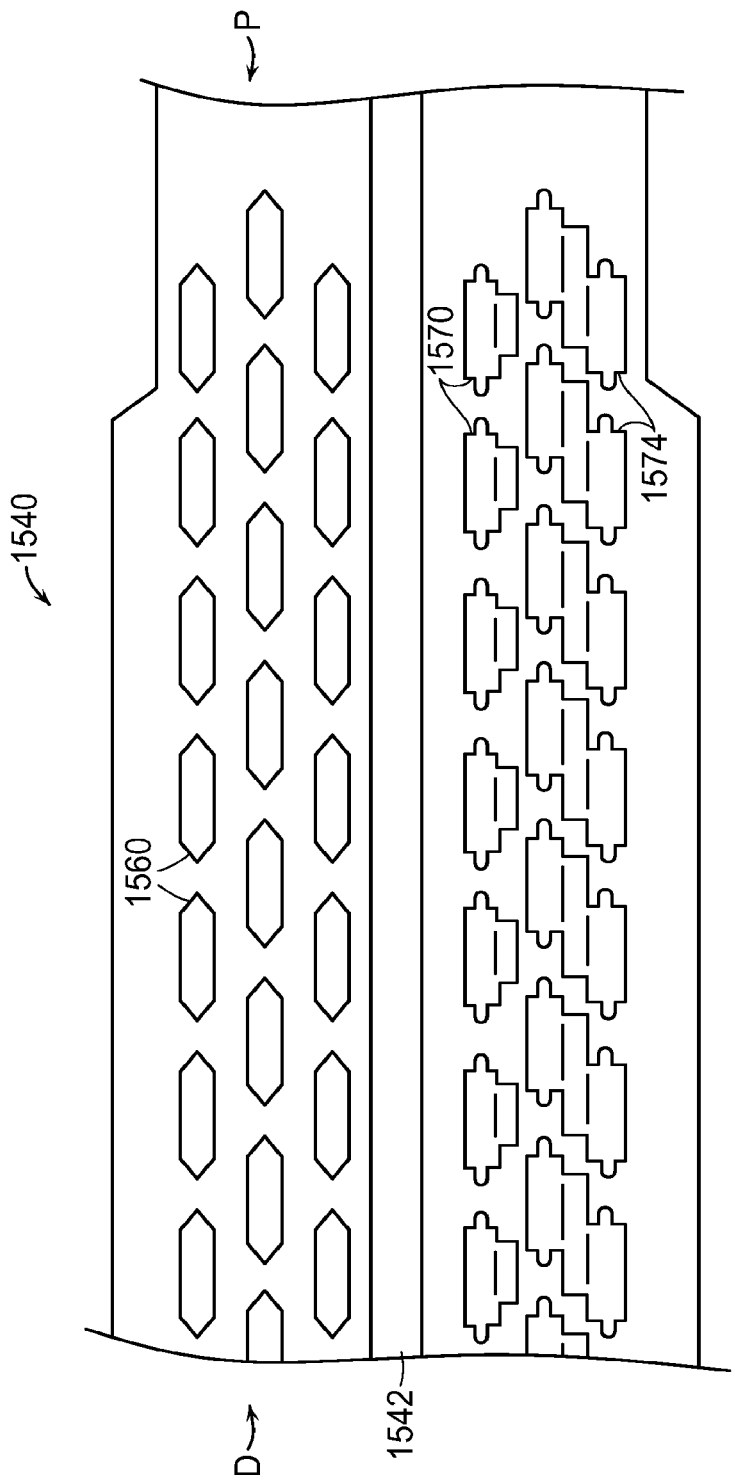
FIG. 18 is a partial top break-away view of a staple cartridge assembly comprising a driver arrangement.

FIG. 18 depicts a staple cartridge 1540 comprising a proximal end P and a distal end D. Staple cartridge 1540 comprises a row of single staple drivers 1570 and a row of double staple drivers 1574. The drivers 1570 lift the innermost row of staples and the drivers 1574 lift the intermediate and outermost rows of staples. The drivers 1570 move independently of the staple drivers 1574. The configuration of the sled that lifts the drivers 1570 and 1574 can determine the manner in which they are lifted relative to each other. For instance, the sled can be configured to lift the drivers 1570 in a leading manner, i.e., the sled can lift a driver 1570 and a driver 1574 concurrently but the driver 1574 being lifted is positioned proximally with respect to the driver 1570 being lifted. In other circumstances, the sled can be configured to lift the drivers 1570 in a lagging manner, i.e., the sled can lift a driver 1570 and a driver 1574 concurrently but the driver 1574 being lifted is positioned distally with respect to the driver 1570 being lifted. Depending on the configuration that is used, the fluid in the tissue being stapled can be pushed in a desired direction.

Figure 19:
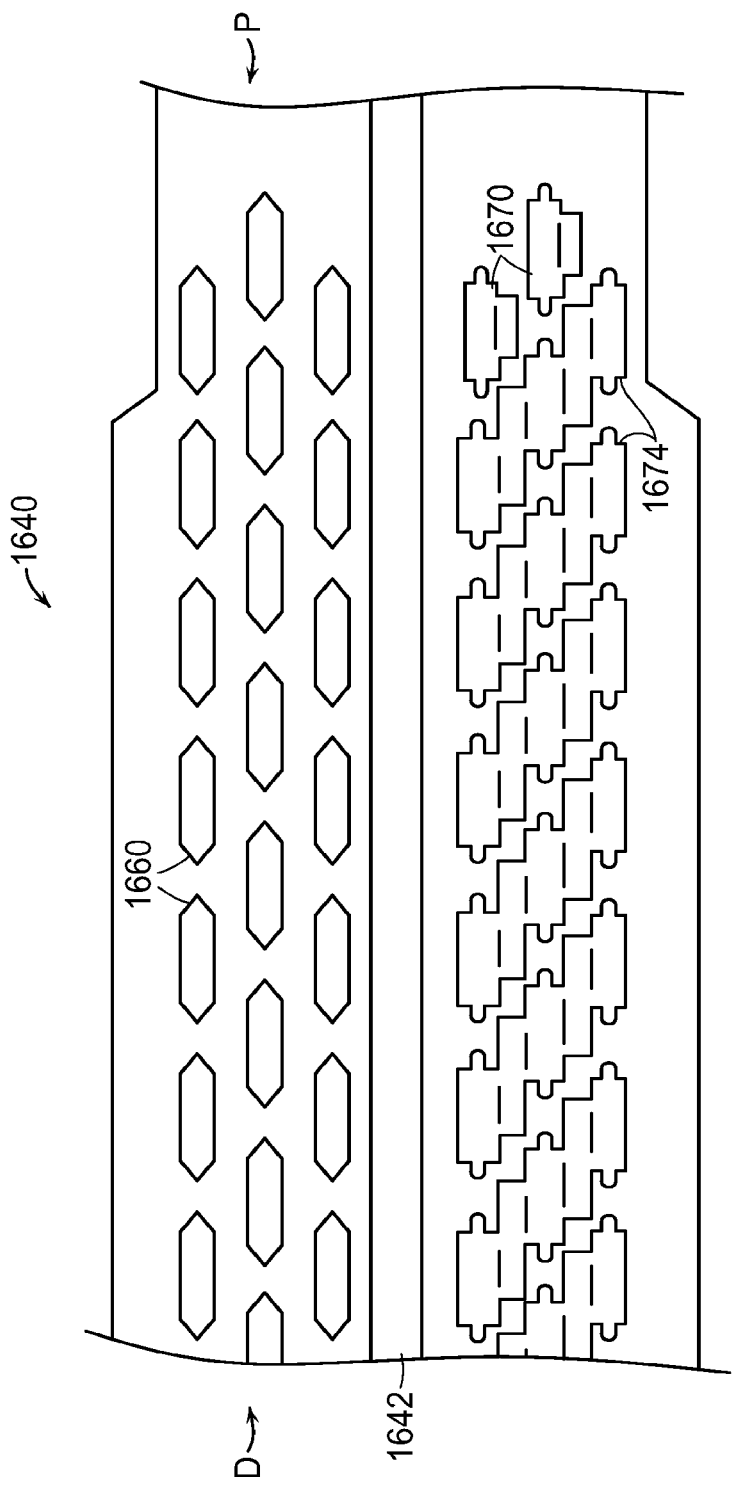
FIG. 19 is a partial top break-away view of a staple cartridge assembly comprising a driver arrangement.

FIG. 19 depicts a staple cartridge 1640 comprising a proximal end P, a distal end D, and staple cavities 1660. Staple cartridge 1640 further comprises single staple drivers 1670 which support one staple and triple staple drivers 1674 which support three staples. The singles staple drivers 1670 are positioned proximally and move independently with respect to the triple staple drivers 1674. The triple staple drivers 1674 can be referred to as tri-staple drivers. As discussed above, the proximal staples of a staple line can overlap with the distal staples of another staple line when more than one staple cartridge is used to complete a series of stapled incisions. Such an overlap can increase the force needed to fire the staples and, in some instances, can cause the overlapping staples to be underformed. Staple underforming can occur when the staple driver lifting the overlapped staple cannot be lifted completely by the sled and/or becomes jammed. In such circumstances, however, the other staples supported by the underlifted or jammed staple driver may not be completely formed as well. If, however, the proximal-most staple drivers only support one staple thereon, the underforming of the staples may be limited to only one staple and the benefits that can be achieved by using staple drivers which fire more than one staple can be achieved by employing such multi-staple drivers distally with respect to the single staple drivers. In some instances, the proximal-most staple of each staple row can be lifted independently of the other staples in that row and independently of the staples in the other rows. Moreover, a concentrated force can be applied to a single staple driver 1670 which, as a result, is more apt to overcome the restrictions that it experiences. In addition, the single staple drivers 1670 can adjust laterally relative to the other drivers which reduces the risk of a complete jam of the staple cartridge 1640. These benefits could also be achieved by using single staple drivers at the distal end of the staple pattern.

Figure 20:
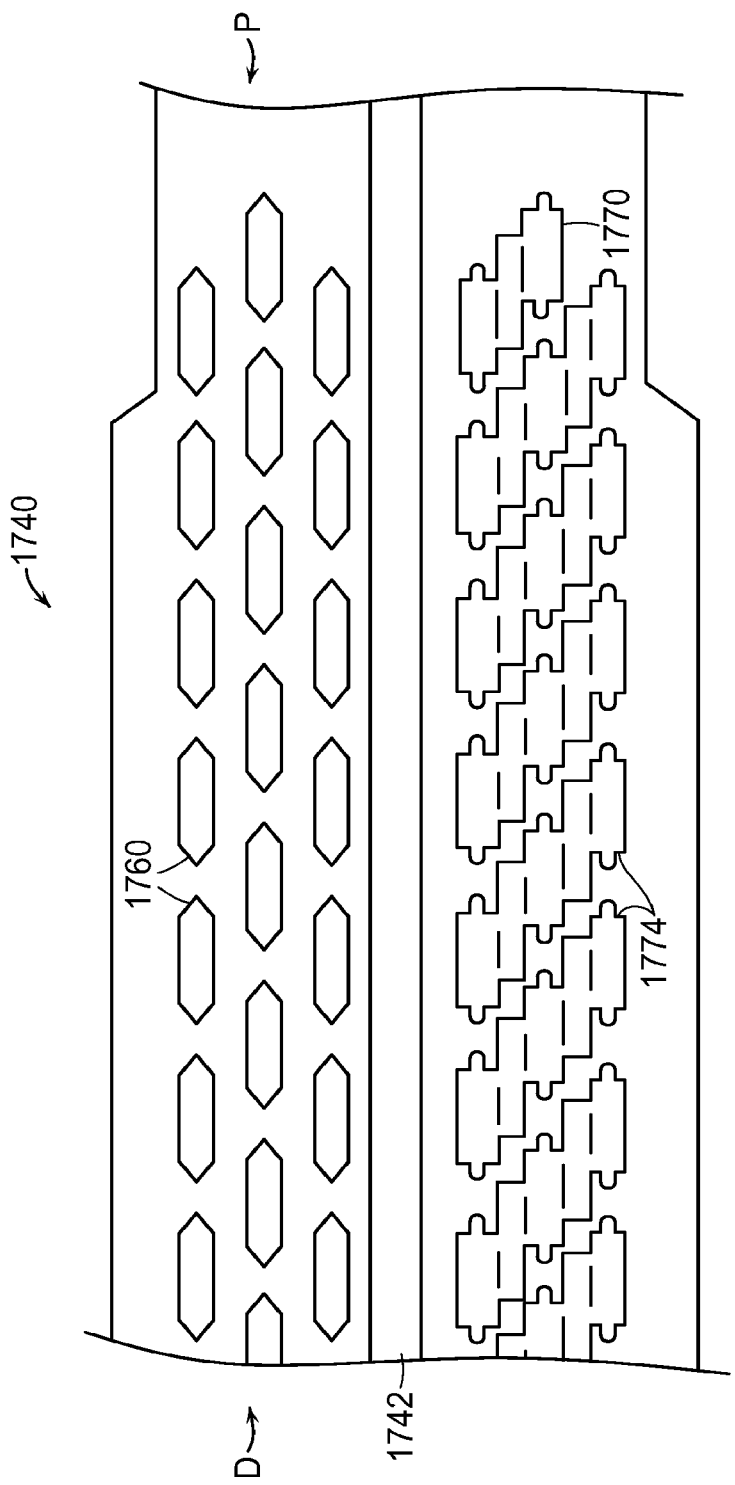
FIG. 20 is a partial top break-away view of a staple cartridge assembly comprising a driver arrangement.

FIG. 20 depicts a staple cartridge 1740 which is similar to the staple cartridge 1640 depicted in FIG. 19; however, the proximal staple drivers 1770 of the staple cartridge 1740 support two staples rather than a single staple. The two staples supported by each staple driver 1770 are in the innermost and intermediate staple rows. As depicted in FIG. 20, the proximal-most staple in the intermediate row of staples is the most proximally positioned staple in the staple pattern deployed by the staple cartridge 1740 and, thus, may be the staple which is most likely to be double-stapled. In the event that the proximal-most staple in the intermediate row is underformed as a result of the double-stapling, the staple driver 1770 may also underform the proximal-most staple in the innermost row. Such underforming of the proximal-most staple in the innermost row can be compensated for by the overlapping proximal-most staple in the outermost row which is formed by a different staple driver such as distal staple driver 1774, for example. The distal staple drivers 1774 form an arrow pattern with each distal staple driver 1774 configured to deform an innermost staple which leads an intermediate staple which leads an outermost staple.

Figure 21:
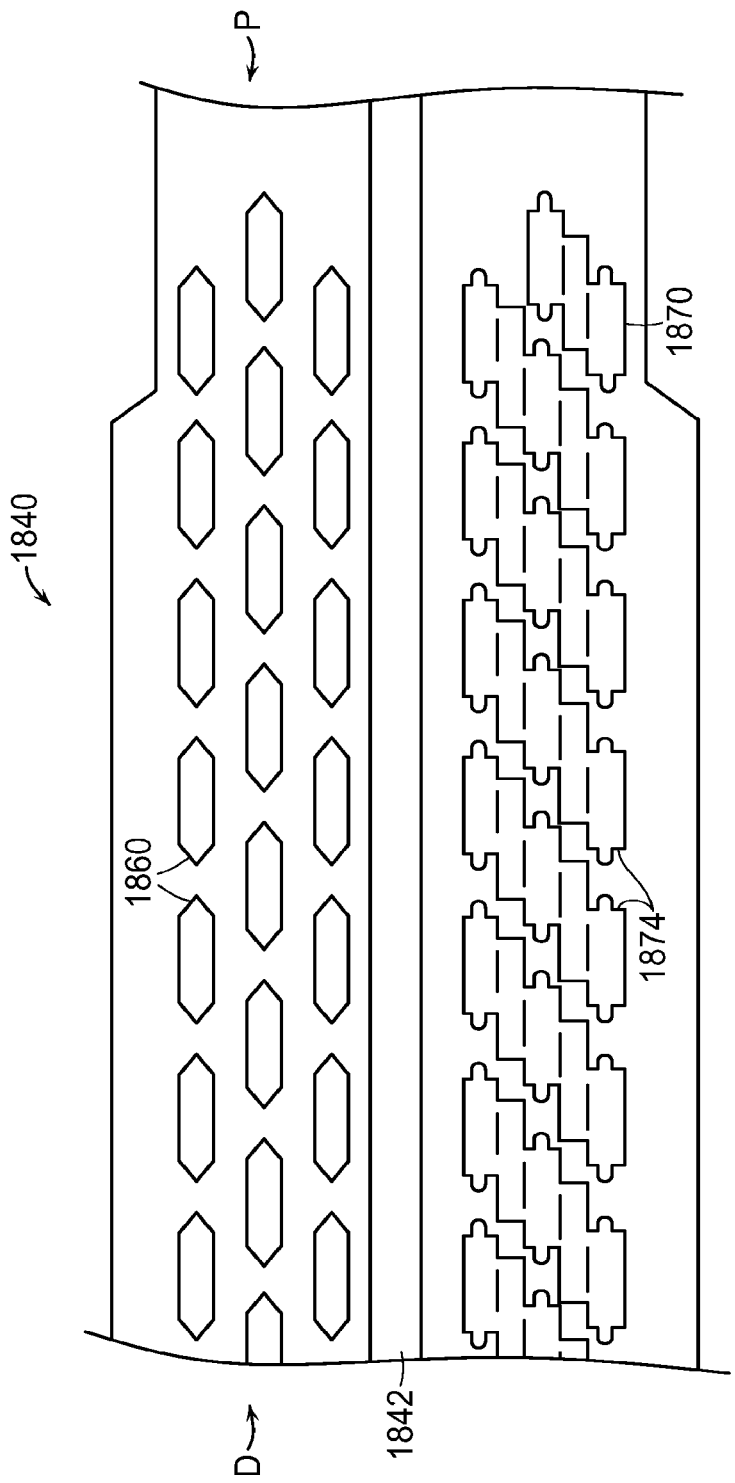
FIG. 21 is a partial top break-away view of a staple cartridge assembly comprising a driver arrangement.

FIG. 21 depicts a staple cartridge 1840 which is similar to the staple cartridge 1740 depicted in FIG. 20; however, the two staples supported by each staple driver 1870 are in the outermost and intermediate staple rows. As depicted in FIG. 21, the proximal-most staple in the intermediate row of staples is the most proximally positioned staple in the staple pattern deployed by the staple cartridge 1840 and, thus, may be the staple which is most likely to be double-stapled. In the event that the proximal-most staple in the intermediate row is underformed as a result of the double-stapling, the staple driver 1870 may also underform the proximal-most staple in the outermost row. Such underforming of the proximal-most staple in the outermost row can be compensated for by the overlapping proximal-most staple in the innermost row which is formed by a different staple driver such as distal staple driver 1874, for example. The distal staple drivers 1874 form a V-shaped pattern with each distal staple driver 1874 configured to deform an outermost staple which leads an intermediate staple which leads an innermost staple.

FIG. 22 depicts a staple cartridge 1940 comprising a proximal end P, a distal end D, and a plurality of staple cavities 1960. The staple cartridge 1940 utilizes a staple driver configuration comprising drivers 1970 and 1972 which is similar to the configuration used by staple cartridge 1840 of FIG. 21; however, the staple cartridge 1940 further incorporates the benefit of single distal staple drivers 1974. Each single distal staple driver 1974 supports a staple prior to the firing cycle. The distal staple drivers 1974 comprise a cluster of four staple drivers which deploys four staples. This cluster includes the distal-most staple cavities in the innermost row, the intermediate row, and the outermost row of staples. The cluster also includes a second staple cavity in one of the three rows of staples. Certain benefits can be achieved by utilizing the single distal staple drivers 1974. For instance, in the event that the actuation sled is prevented from completing the firing cycle due to some impediment, it is more advantageous to leave a single distal staple driver 1974 unfired rather than have a staple driver configured to fire more staples remain unfired.

FIG. 23 depicts a staple cartridge 2040 comprising a plurality of single staple drivers. The plurality of single staple drivers comprises first staple drivers 2070, second staple drivers 2072, and third staple drivers 2074. The third staple drivers 2074 are arranged in a row located nearest the knife slot 2042, the second staple drivers 2072 are arranged in a row adjacent the row of third staple drivers 2074, and the first staple drivers 2070. The third staple drivers 2074 are lifted within the staple cartridge 2040 by a first camming member of an actuation sled. The third staple drivers 2074 include cam surfaces which are aligned with one another such that the first camming member can engage the cam surfaces as the first camming member moves along a firing path. The first staple drivers 2070 and the second staple drivers 2072 are lifted within the staple cartridge 2040 by a second camming member of the actuation sled. The first staple drivers 2070 and the second staple drivers 2072 include cam surfaces which are aligned with one another such that the second camming member can engage the cam surfaces as the second camming member moves along a firing path. Alternative arrangements are contemplated where an actuation sled includes a first camming member which engages first cam surfaces on the first staple drivers, a second camming member which engages second cam surfaces on the second staple drivers, and a third camming member which engages third cam surfaces on the third staple drivers.

Figure 24:
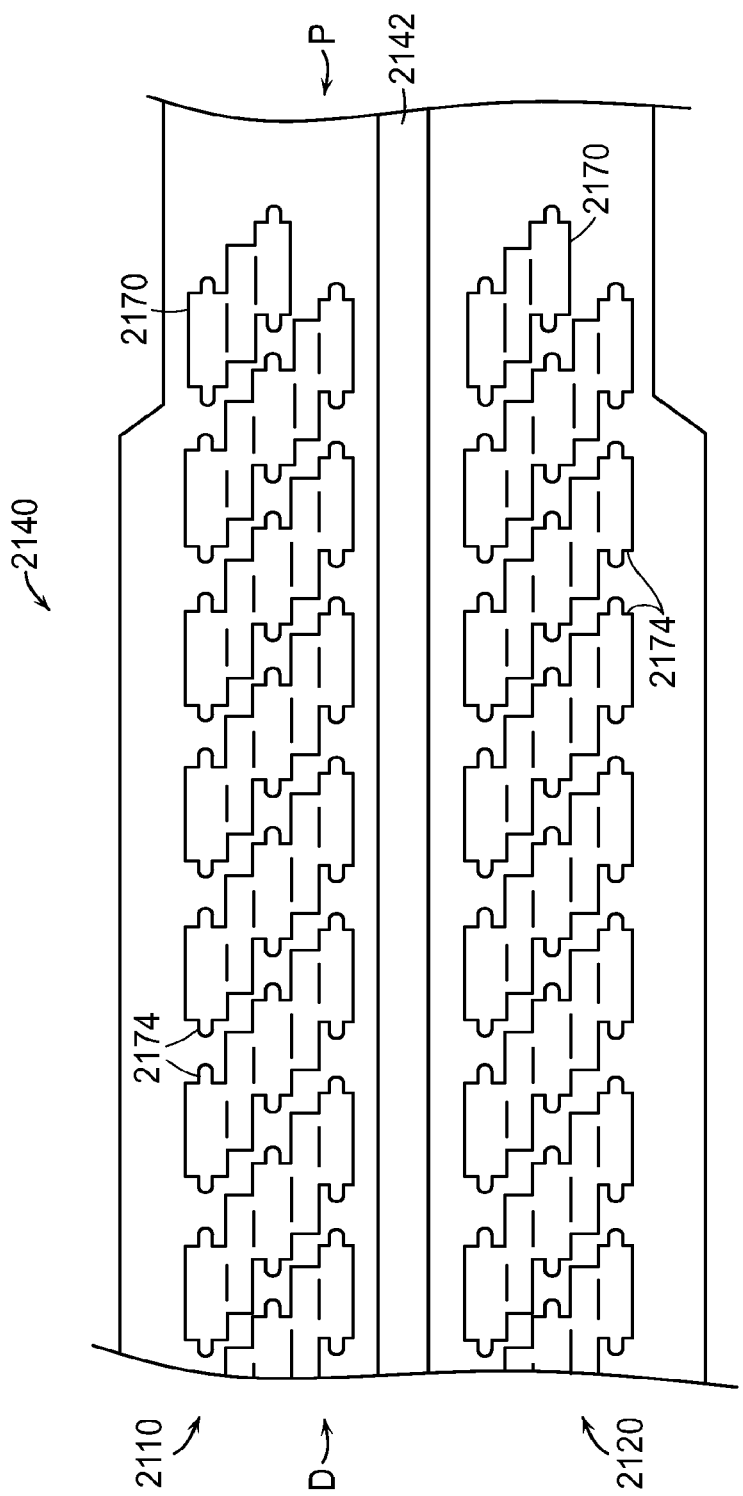
FIG. 24 is a partial top break-away view of a staple cartridge assembly comprising a driver arrangement.

FIG. 24 depicts a staple cartridge 2140 comprising a proximal end P and a distal end D. Staple cartridge 2140 further comprises double staple drivers 2170 which support two staples and triple staple drivers 2174 which support three staples. Staple drivers 2174 can be referred to as tri-staple drivers. A knife channel 2142 separates a first side 2110 and a second side 2120 of the staple cartridge 2140. The first side 2110 of the staple cartridge 2140 comprises staple drivers configured to eject the outer most staple row first, or in a leading manner. The second side 2120 of staple cartridge 2140 comprises staple drivers configured to eject the inner most staple row first, or in a leading manner. In contrast to the "V" shape and arrow patterns discussed above, the combination of the first side 2110 and the second side 2120 staple driver configuration creates a "wave" pattern as the staples are being deployed during a firing cycle. More particularly, the deployment of the staples from the first side 2110 pushes fluid within the tissue toward the knife channel 2142 while the deployment of the staples from the second side 2120 pushes fluid within the tissue away from the knife channel 2142.

Figure 25:
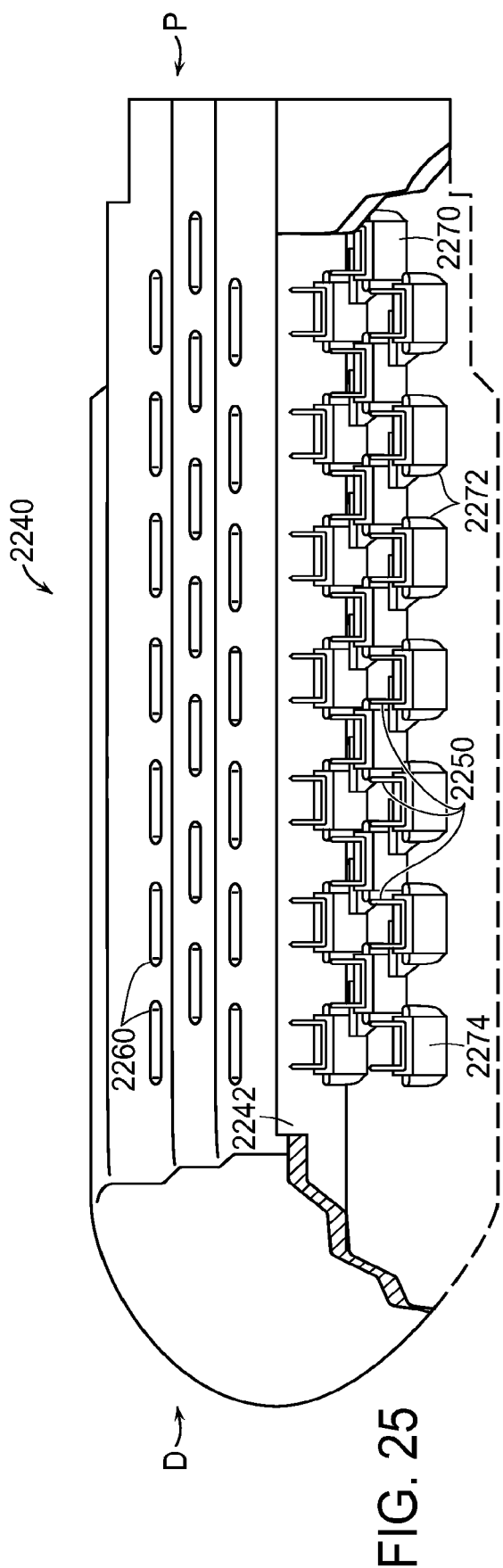
FIG. 25 illustrates a staple cartridge assembly with portions broken away for the purposes of illustrating a staple driver and staple arrangement.
Figure 26:
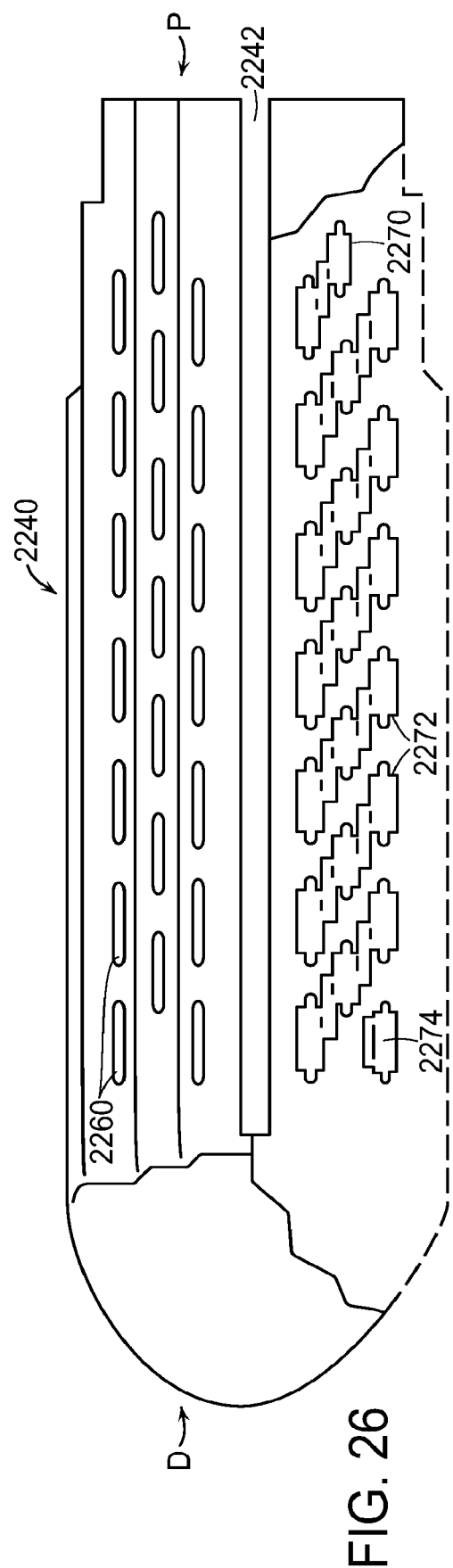
FIG. 26 is a top break-away view of the staple cartridge assembly of FIG. 25.

FIGS. 25 and 26 depict a staple cartridge 2240 comprising a proximal end P and a distal end D. Staple cartridge 2240 is configured to eject staples in an arrow pattern, discussed above. Staple cartridge 2240 comprises proximal staple drivers 2270 which support two staples, central staple drivers 2272 which support three staples and orphanable staple drivers 2274 which support one staple. Central staple drivers 2272 can be referred to as tri-staple drivers. As the orphanable staple drivers 2274 comprise a single staple driver in a pattern of multi-staple drivers, the impact of these drivers not being fully-fired is reduced. While such orphanable drivers have utility at the proximal and distal ends of a staple cartridge in accordance with the teachings provided herein, a staple driver pattern can include an orphanable staple driver at any desirable location, especially at a location where the staple driver may be prohibited from being fully lifted within the staple cartridge. In various instances, the staple associated with an orphanable staple driver can be laterally aligned with another staple in the staple pattern.

Figure 27:
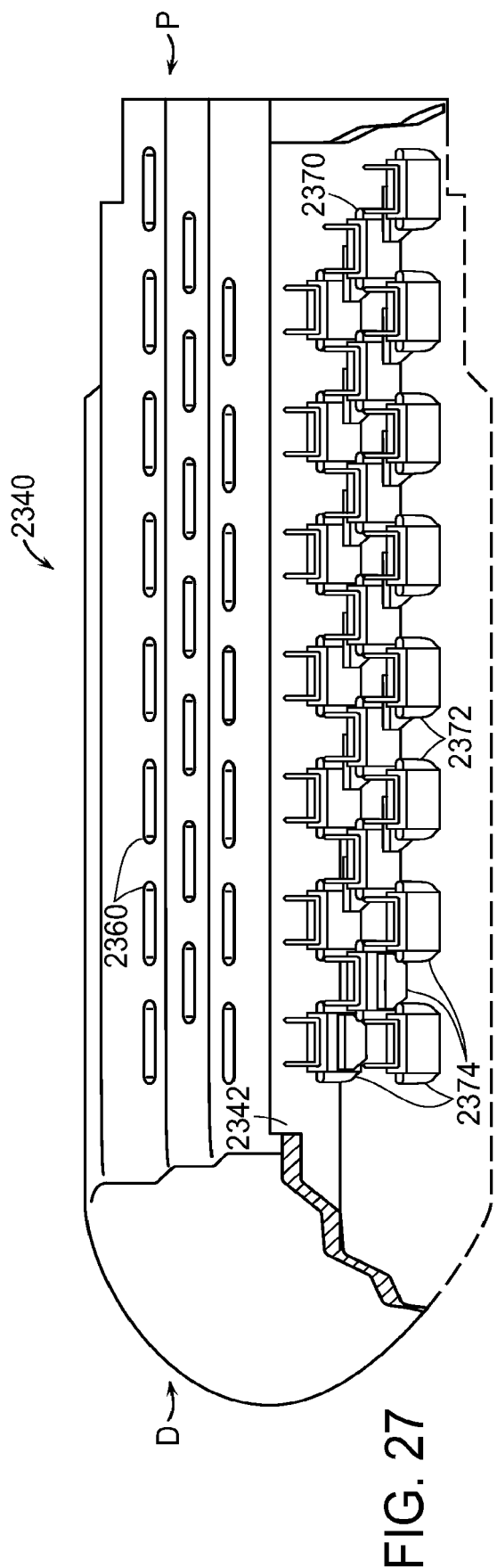
FIG. 27 illustrates a staple cartridge assembly with portions broken away for the purposes of illustrating a staple driver and staple arrangement.
Figure 28:
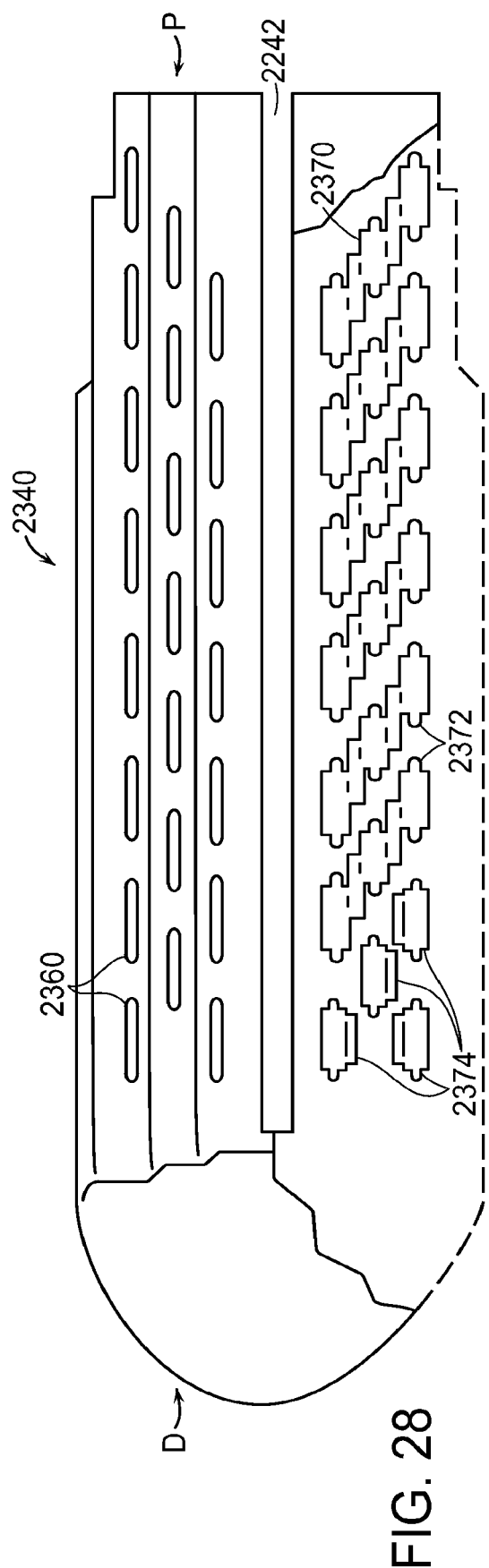
FIG. 28 is a top break-away view of the staple cartridge assembly of FIG. 27.

FIGS. 27 and 28 depict a staple cartridge 2340 comprising a proximal end P and a distal end D. The staple cartridge 2340 is configured to eject staples in an arrow pattern, discussed above. Staple cartridge 2340 comprises proximal staple drivers 2370 comprising three staple supporting features, central staple drivers 2372 which support three staples, and distal staple drivers 2374 which support one staple each. Drivers 2370 and 2372 can be referred to as tri-staple drivers. The proximal staple driver 2370 comprises an empty staple retaining feature. When the proximal staple driver 2370 is lifted upwardly by an actuation sled, the empty staple retaining feature extends above the deck of the staple cartridge. This permits the empty staple retaining feature to engage the tissue and provide for an additional holding or clamping force to maintain the position of the tissue between the staple cartridge 2340 and an anvil (not shown). In addition to the above, the empty staple driver may reduce the likelihood of double stapling of a subsequent staple line, as discussed above.

Figure 29:
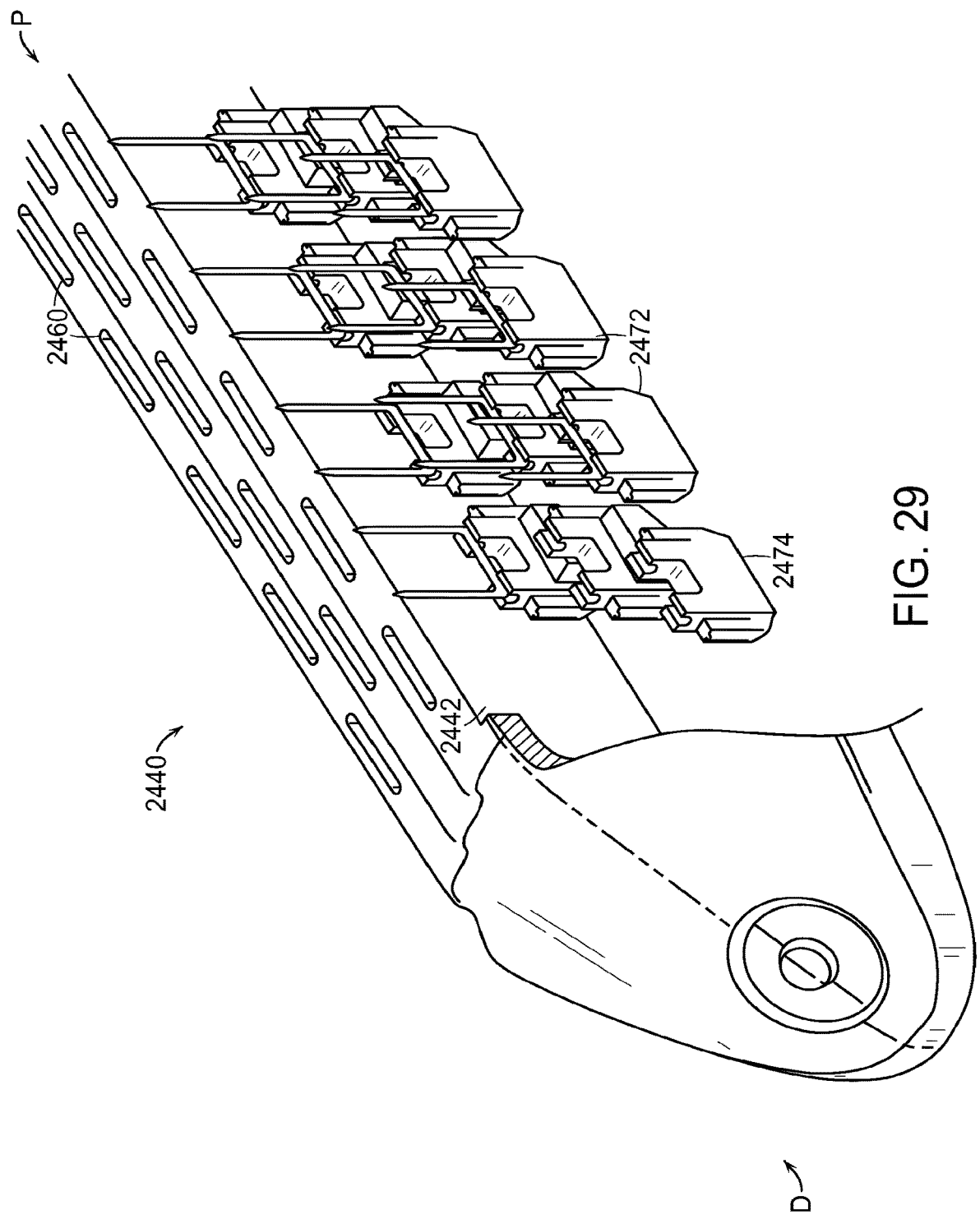
FIG. 29 is a partial break-away perspective view of a staple cartridge assembly.

FIG. 29 depicts a staple cartridge 2440 comprising a proximal end P and a distal end D. Staple cartridge 2440 further comprises central staple drivers 2472 which support three staples and distal staple drivers 2474 comprising three staple supporting features. Staple drivers 2472 and 2474 can be referred to as tri-staple drivers. The distal staple drivers 2474, however, are configured to only releasably retain one staple. While the empty staple supporting features described in previous embodiments are configured to extend above the surface of the deck to engage the tissue, that is not the case in the present embodiment. In fact, the empty staple retaining features may remain below the staple cartridge deck, or may not even have separate staple cavities. While it may be counterintuitive to have staple supporting features that are not configured to support staples, this feature provides for a symmetrical staple driver configuration and interaction with the actuation sled (not shown) to symmetrically engage each staple driver. This reduces the likelihood of an actuation sled misengaging an asymmetrical staple driver and causing the staple cartridge to either jam or not completely fire. The symmetrical staple driver configuration also permits the even distribution of firing forces to be applied to the staple drivers by the actuation sled. Furthermore, in the event the distal staple drivers 2474 are prevented from firing, the effect of the distal staple driver 2474 not firing is greatly reduced as it would result in only a single staple not firing rather than a greater amount of staples fired by such a driver.

FIGS. 30-39 depict staple cartridges and drivers comprising the arrow pattern of staple formation, discussed above; however, they are not limited to such a pattern of staple formation. Other patterns can be used, such as the wedge and/or wave patterns discussed above, for example.

Figure 30:
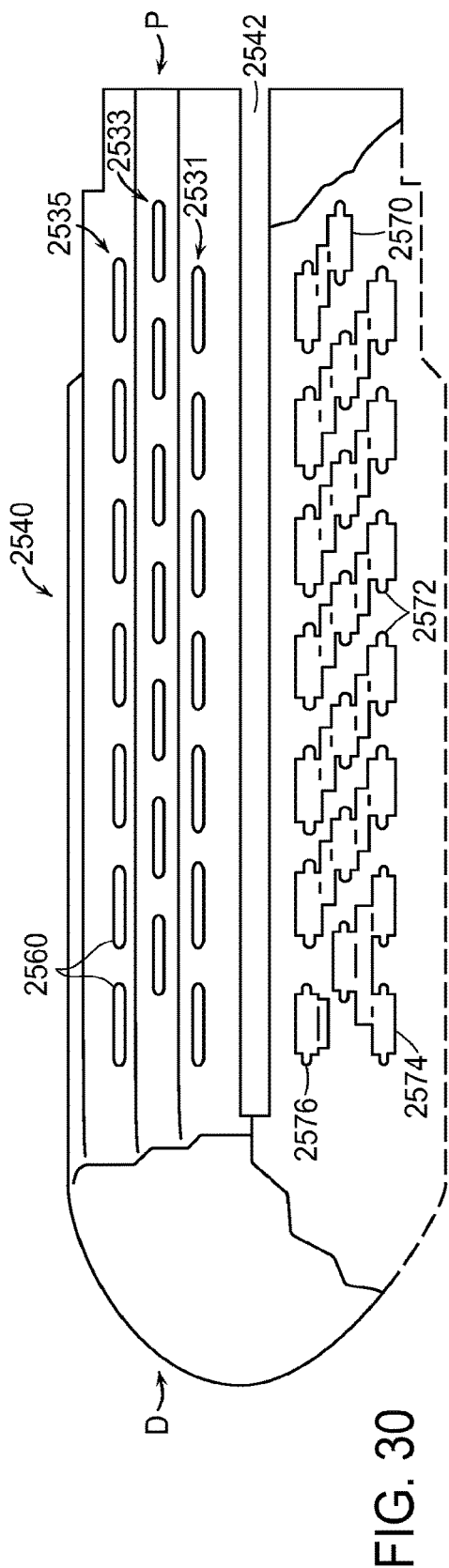
FIG. 30 is a top break-away view of a staple cartridge assembly illustrating a staple driver and staple arrangement.
Figure 31:
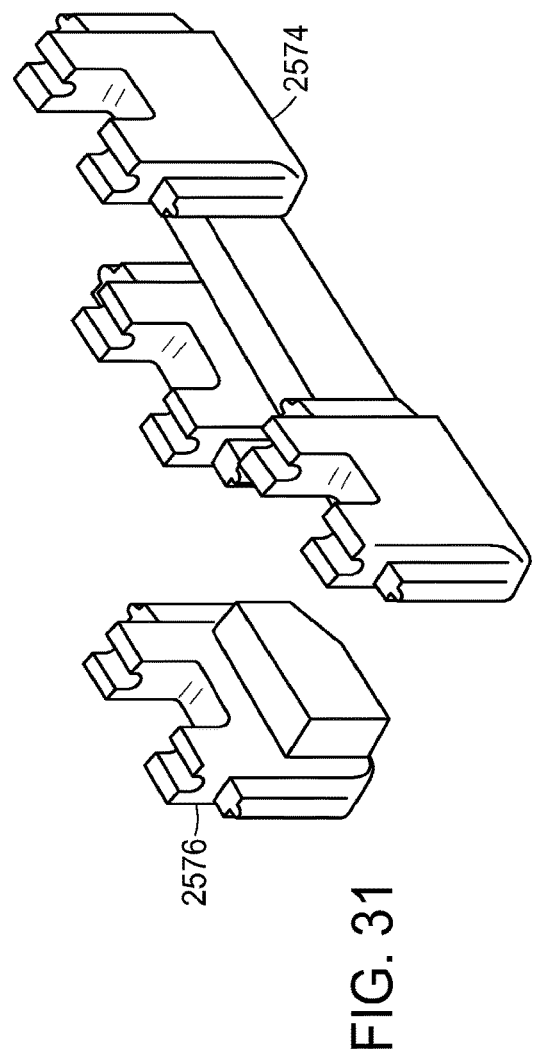
FIG. 31 is a perspective view of the staple driver arrangement of FIG. 30.

FIGS. 30 and 31 depict a staple cartridge 2540 comprising a proximal end P, a distal end D, a knife channel 2542, and a plurality of staple cavities 2560. Staple cartridge 2540 further comprises a plurality of staple drivers including drivers 2570, 2572, 2574, and 2576. The proximal staple drivers 2570 support two staples. Central staple drivers 2572 support three staples. Outer distal staple drivers 2574 also support three staples, albeit in a different configuration than the central staple drivers 2572. Staple drivers 2572 and 2574 can be referred to as tri-staple drivers. The central staple drivers 2572 support a staple in an inner row 2531 of staple cavities, a staple in an intermediate row 2533 of staple cavities, and a staple in an outer row 2535 of staple cavities. On the other hand, the outer distal staple drivers support two staples from the same row and a third staple in another row. The outer distal staple driver 2574 therefore has an asymmetrical configuration compared to the symmetrical central staple drivers 2572. The inner distal staple drivers 2576 support one staple.

In various instances, the inner distal staple drivers 2578 may be configured to deploy a staple which comprises a marker staple. This marker staple may be unique in character wherein the proper deformation of this marker staple can indicate that the staple cartridge was completely and/or correctly fired, for example. In addition, the marker staple may be of a color or characteristic that creates a visual marker for the surgeon to align the subsequent staple cartridge. By having an inner distal staple driver 2576 comprising a single staple, for example, there is a better likelihood that the distal staple will be ejected and completely form since a single staple driver requires less force to eject than a staple driver comprising multiple staples. As discussed above, the outer distal staple driver 2574 ejects two staples from the outer row. Owing to the simultaneous formation of two staples in the outer row, a better hemostatic outer boundary can be created. Such an arrangement, used in conjunction with a compression barrier, for instance, may reduce bleeding of the tissue at the distal end of the cutting stroke.

Figure 32:
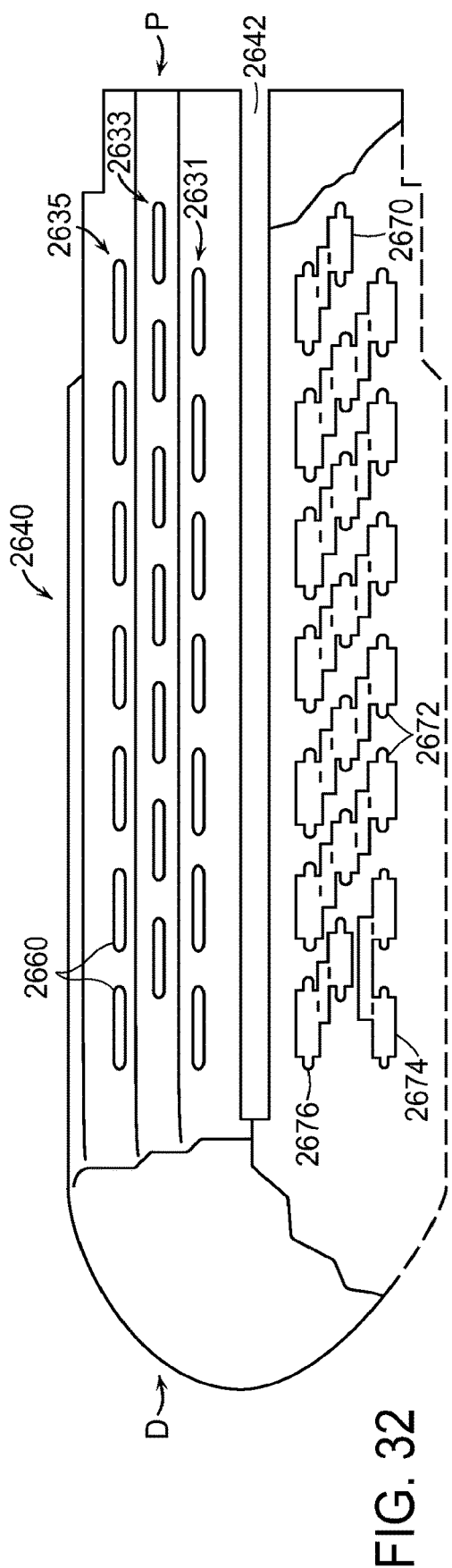
FIG. 32 is a top break-away view of a staple cartridge assembly illustrating a staple driver and staple arrangement.
Figure 33:
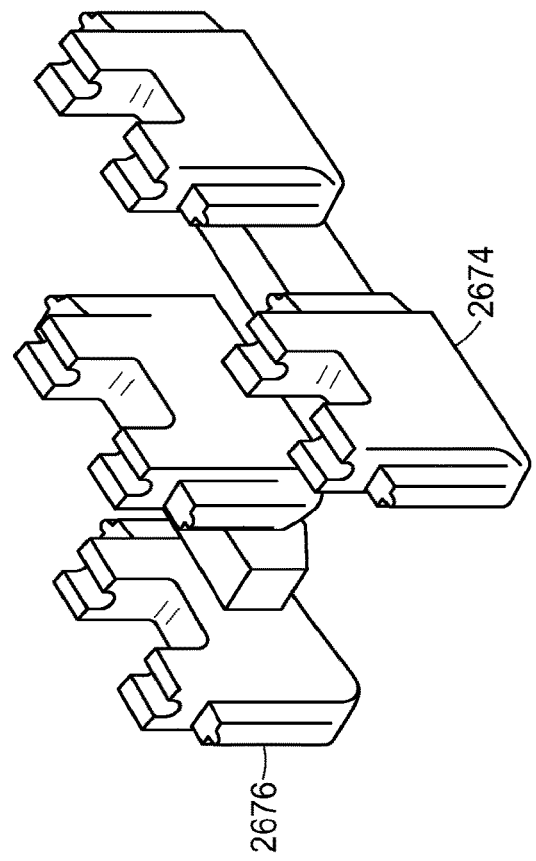
FIG. 33 is a perspective view of the staple driver arrangement of FIG. 32.

FIGS. 32 and 33 depict a staple cartridge 2640 comprising a proximal end P, a distal end D, a knife channel 2642, and a plurality of staple cavities 2660. Staple cartridge 2640 further comprises a plurality of staple drivers including drivers 2670, 2672, 2674, and 2676. Proximal staple drivers 2670 support two staples. Central staple drivers 2672 support three staples. Central staple drivers 2672 can be referred to as tri-staple drivers. Outer distal staple drivers 2674 support two staples in the same row of staples, such as in outer row 2635 of staples, for example. Inner distal staple drivers 2676 support two staples, a staple in the inner row 2631 of staples and a staple in the middle row 2633 of staples. The outer distal staple drivers 2674 and the inner distal staple drivers 2676 can co-operate to deploy a distal cluster of four staples. In certain instances, the outer staple drivers 2674 can be deployed in a leading manner to the inner staple drivers 2676. In other instances, the outer staple drivers 2674 can be deployed in a lagging manner to the inner staple drivers 2676. While, in some instances, the inner staple drivers 2676 and the outer staple drivers 2674 can be deployed simultaneously.

Figure 34:
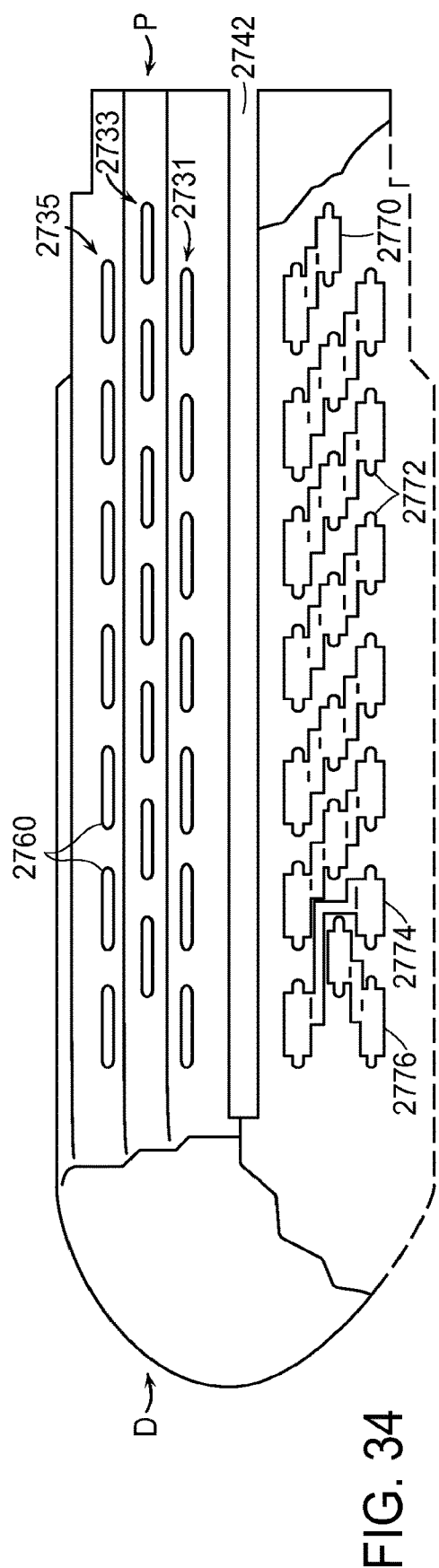
FIG. 34 is a top break-away view of a staple cartridge assembly illustrating a staple driver and staple arrangement.
Figure 35:
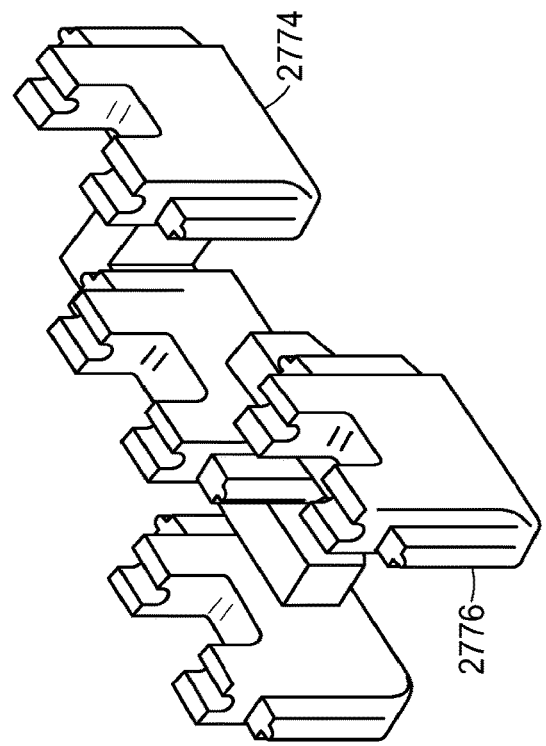
FIG. 35 is a perspective view of the staple driver arrangement of FIG. 34.

FIGS. 34 and 35 depict a staple cartridge 2740 comprising a proximal end P, a distal end D, a knife channel 2742, and a plurality of staple cavities 2760. Staple cartridge 2740 further comprises a plurality of staple drivers including drivers 2770, 2772, 2774, and 2776. Proximal staple drivers 2770 support two staples. Central staple drivers 2772 support three staples. Central staple drivers 2772 can be referred to as tri-staple drivers. First distal staple drivers 2774 support two staples, i.e., one staple in an inner row of staples 2731 and another staple in an outer row of staples 2735. In this way, the first distal staple drivers 2774 support staples which are laterally offset.

Furthermore, the staples supported by the first distal staple driver 2774 are longitudinally offset. The second distal staple drivers 2776 support two staples, i.e., a staple in the outer row of staples 2735 and a staple in an intermediate row of staples 2733. The staples supported by the drivers 2776 are longitudinally offset as well. The staples supported by a first distal driver 2774 and a second distal driver 2776 comprise a distal cluster of four staples. The first distal staple driver 2774 is configured such that when the actuation sled translates distally, the staple positioned in the inner row 2731 of the distal cluster is ejected from the staple cartridge 2740 before the staples supported by the second distal driver 2776 are ejected from the staple cartridge 2740. In this way, the first distal staple driver 2774 can finish the formation of the inner staple row 2731 before finishing the formation of the intermediate row 2733 and the outer row 2735. Such an arrangement can improve the hemostasis of the incision.

Figure 36:
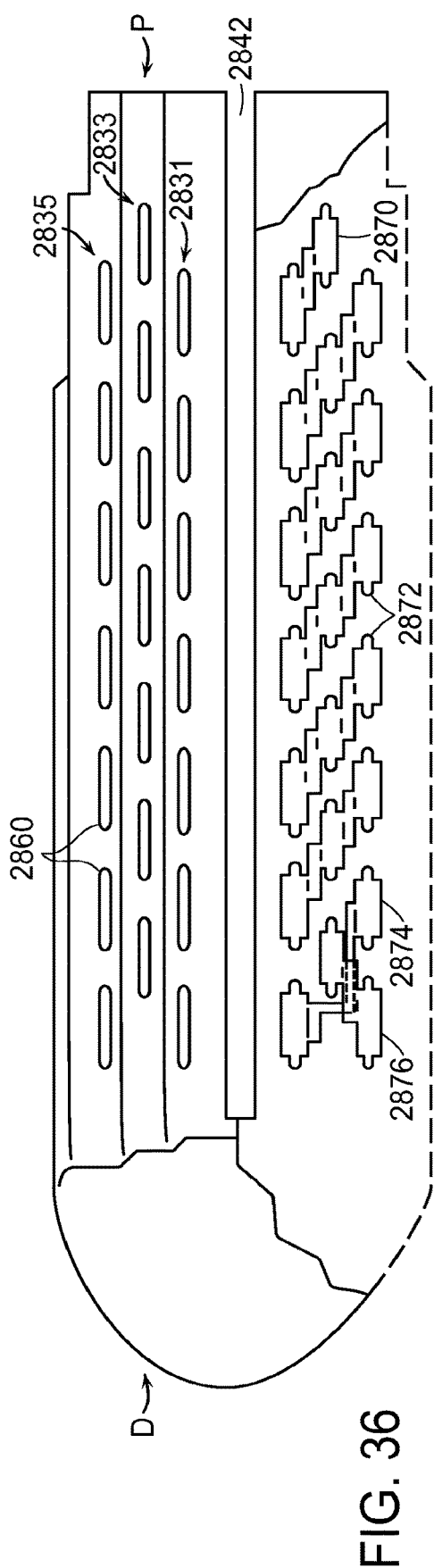
FIG. 36 is a top break-away view of a staple cartridge assembly illustrating a staple driver and staple arrangement.
Figure 37:
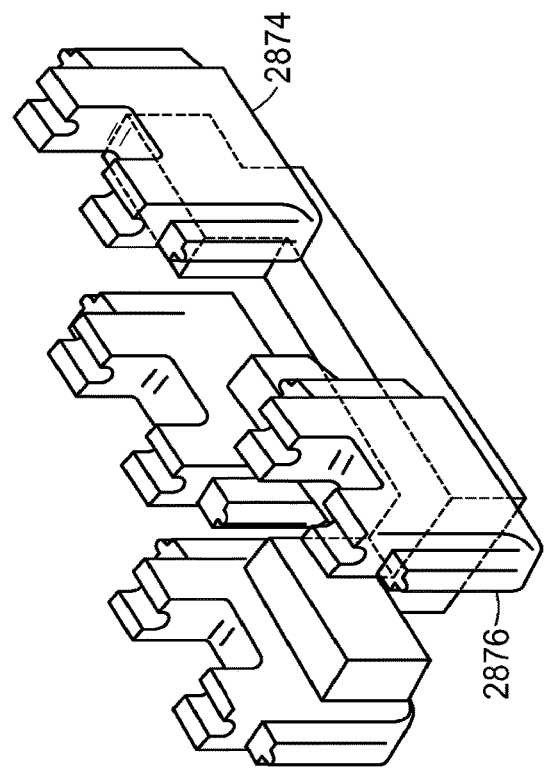
FIG. 37 is a perspective view of the staple driver arrangement of FIG. 36.

FIGS. 36 and 37 depict a staple cartridge 2840 comprising a proximal end P, a distal end D, a knife channel 2842, and a plurality of staple cavities 2860. Staple cartridge 2840 further comprises a plurality of staple drivers including drivers 2870, 2872, 2874, and 2876. Proximal staple drivers 2870 support two staples. Central staple drivers 2872 support three staples. Central staple drivers 2872 can be referred to as tri-staple drivers. First distal staple drivers 2874 support two staples, i.e., one staple in an inner row of staples 2831 and one staple in an outer row of staples 2835. In this way, the first distal staple drivers 2874 support staples which are laterally offset. Furthermore, the staples supported by the first distal staple driver 2774 are longitudinally offset. The second distal staple drivers 2876 support two staples, i.e., a staple in the outer row of staples 2835 and a staple in an intermediate row of staples 2833. The staples supported by the drivers 2876 are longitudinally offset as well. The staples supported by a first distal driver 2874 and a second distal driver 2876 comprise a distal cluster of four staples. The first distal staple driver 2874 is configured such that when the actuation sled translates distally, the staple positioned in the inner row 2831 of the distal cluster is ejected from the staple cartridge 2840 before the staples supported by the second distal driver 2876 are ejected from the staple cartridge 2840. In this way, the first distal staple driver 2874 can finish the formation of the inner staple row 2831 before finishing the formation of the intermediate row 2833 and the outer row 2835. Such an arrangement can improve the hemostasis of the incision.

Referring again to FIGS. 36 and 37, the first and second distal staple drivers 2874, 2876 are configured in an overlap/underlap configuration. This feature may provide additional stability of the distal staple drivers 2874, 2876 as compared to the wraparound configuration of the distal staple drivers 2774, 2776 disclosed in FIGS. 34 and 35. In any event, both configurations permit the independent firing of the two staple drivers in comparison to a distal staple driver which drives four staples. The two independent first and second distal staple drivers thus reduces the amount of force required to fire each distal staple driver independently and in the event that one of the distal staple drivers is not fully ejected, reduces the number of underformed staples and results in a more secure staple line formation.

Figure 38:
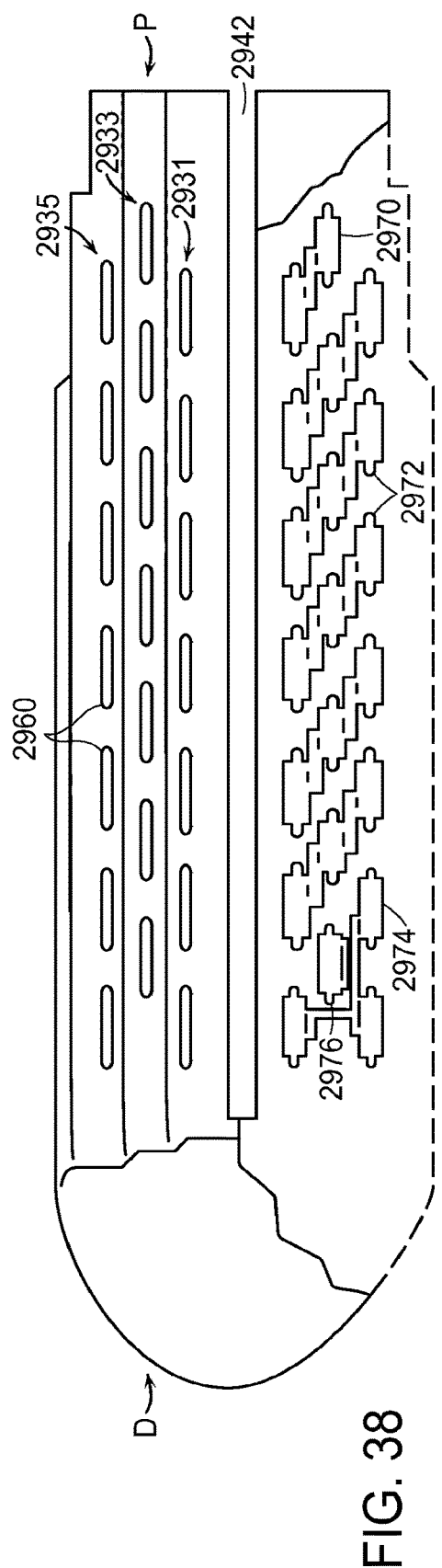
FIG. 38 is a top break-away view of a staple cartridge assembly illustrating a staple driver and staple arrangement.
Figure 39:
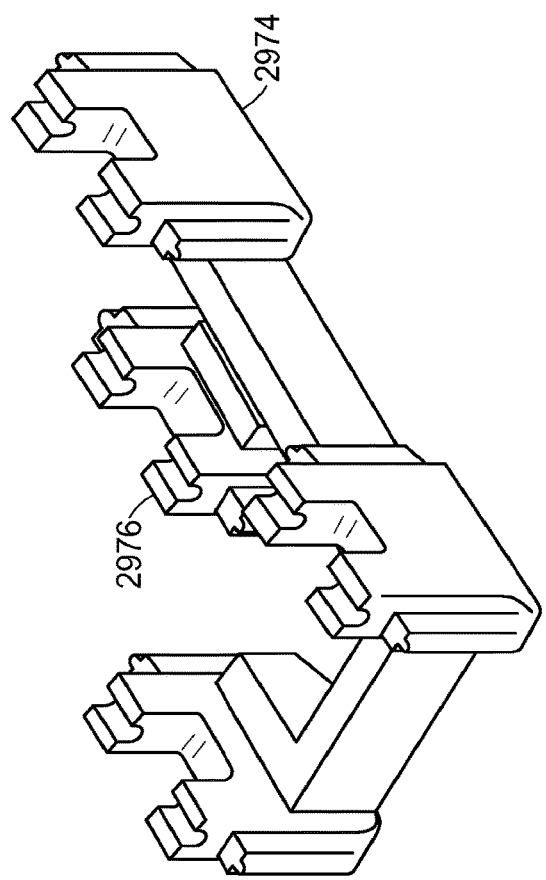
FIG. 39 is a perspective view of the staple driver arrangement of FIG. 38.

FIGS. 38 and 39 depict a staple cartridge 2940 comprising a proximal end P, a distal end D, a knife channel 2942, and a plurality of staple cavities 2960. Staple cartridge 2940 further comprises a plurality of staple drivers including drivers 2970, 2972, 2974, and 2976. Proximal staple drivers 2970 support two staples. Central staple drivers 2972 support three staples. L-shaped distal staple drivers 2974 also support three staples, i.e., two staples in the outer row of staples 2935 and one staple and a staple in the inner row of staples 2931. The staple supported the inner row of staples 2931 by the L-shaped distal staple driver 2974 is longitudinally aligned with one of the staples supported by the driver 2974 in the outer row of staples 2935 and longitudinally offset from one of the staples supported by the driver 2974 in the outer row of staples 2935. Staple drivers 2972 and 2974 can be referred to as tri-staple drivers. Drivers 2976 support one staple.

The unique L-shape configuration of the drivers 2974 provides various benefits to improve hemostasis. For instance, the distal staple driver 2974 can be lifted prior to the driver 2976 and, as a result, the staples fired by the distal staple driver 2974 can provide a longitudinal and/or lateral barrier in the tissue which is formed prior to final formation of the staple fired by the driver 2976. This particular staple driver configuration may be utilized at the distal end of a staple line and/or at any location in the staple line. In various instances, a tether or buttress could be connected between the staple in the inner row of staples 2931 releasably supported by the L-shaped distal staple driver 2974 and a staple in the outer row of staples 2935. This arrangement could create a distal hemostasis barrier. Other tether and/or buttress configurations are within the scope of the present disclosure.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES; now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009; now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Patent Application Publication No. 2012/0298719;

U.S. patent application Ser. No. 13/524,049, entitled ARTICULATABLE SURGICAL INSTRUMENT COMPRISING A FIRING DRIVE, filed on Jun. 15, 2012; now U.S. Patent Application Publication No. 2013/0334278;

U.S. patent application Ser. No. 13/800,025, entitled STAPLE CARTRIDGE TISSUE THICKNESS SENSOR SYSTEM, filed on Mar. 13, 2013; now U.S. Patent Application Publication No. 2014/0263551;

U.S. patent application Ser. No. 13/800,067, entitled STAPLE CARTRIDGE TISSUE THICKNESS SENSOR SYSTEM, filed on Mar. 13, 2013; now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although the various embodiments of the devices have been described herein in connection with certain disclosed embodiments, many modifications and variations to those embodiments may be implemented. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A staple cartridge, comprising:
a cartridge body defining a longitudinal slot;
staple cavities defined in the cartridge body on a first lateral side of the longitudinal slot, wherein the staple cavities comprise:
a first row of staple cavities adjacent to the longitudinal slot;
a second row of staple cavities; and
a third row of staple cavities, wherein the second row of staple cavities is between the first row of staple cavities and the third row of staple cavities; and
a first staple driver configured to deploy staples from the second row of staple cavities and the third row of staple cavities, wherein the first staple driver comprises:
a first staple support in the third row of staple cavities;
a second staple support in the second row of staple cavities; and
a third staple support in the third row of staple cavities.

2. The staple cartridge of claim 1, wherein the second staple support is distal to the first staple support and proximal to the third staple support.

3. The staple cartridge of claim 1, further comprising a second staple driver comprising a fourth staple support in the first row of staple cavities.

4. The staple cartridge of claim 3, wherein the fourth staple support is laterally aligned with the third staple support.

5. The staple cartridge of claim 3, wherein the fourth staple support is the only staple support of the second staple driver.

6. The staple cartridge of claim 3, further comprising a staple supported by the fourth staple support, wherein the staple supported by the fourth staple support comprises a marker to provide a visual confirmation to a user that the staple cartridge has completely fired.

7. The staple cartridge of claim 1, further comprising a second staple driver configured to deploy staples from the first row of staple cavities, the second row of staple cavities, and the third row of staple cavities, wherein the second staple driver comprises:
a fourth staple support in the third row of staple cavities;
a fifth staple support in the second row of staple cavities; and
a sixth staple support in the first row of staple cavities.

8. The staple cartridge of claim 7, wherein the sixth staple support is laterally aligned with the first staple support.

9. A staple cartridge, comprising:
a cartridge body defining a longitudinal slot;

staple cavities defined in the cartridge body on a first lateral side of the longitudinal slot, wherein the staple cavities comprise:
- a first row of staple cavities adjacent to the longitudinal slot;
- a second row of staple cavities; and
- a third row of staple cavities, wherein the second row of staple cavities is between the first row of staple cavities and the third row of staple cavities; and a first staple driver, comprising:
- a first cradle to support a first staple in the third row of staple cavities;
- a second cradle to support a second staple in the second row of staple cavities; and
- a third cradle to support a third staple in the third row of staple cavities; and a second staple driver comprising a fourth cradle to support a fourth staple in the first row of staple cavities, wherein the fourth staple is laterally aligned with the third staple.

10. The staple cartridge of claim 9, wherein the fourth staple is the only staple supported by the second staple driver.

11. The staple cartridge of claim 9, wherein the second cradle is distal to the first cradle and proximal to the third cradle.

12. The staple cartridge of claim 9, further comprising the fourth staple, wherein the fourth staple comprises a marker to provide a visual confirmation to a user that the staple cartridge has completely fired.

13. The staple cartridge of claim 9, further comprising a third staple driver, comprising:
- a fifth cradle to support a fifth staple in the third row of staple cavities;
- a sixth cradle to support a sixth cradle in the second row of staple cavities; and
- a seventh cradle to support a seventh staple in the first row of staple cavities.

14. The staple cartridge of claim 13, wherein the seventh cradle is laterally aligned with the first cradle.

15. A staple cartridge, comprising:
a cartridge body defining a longitudinal slot;
- a first row of staple cavities defined in the cartridge body adjacent to the longitudinal slot;
- a second row of staple cavities defined in the cartridge body; and
- a third row of staple cavities defined in the cartridge body, wherein the second row of staple cavities is intermediate the first row of staple cavities and the third row of staple cavities; and a first staple driver configured to deploy staples from the second row of staple cavities and the third row of staple cavities, wherein the first staple driver comprises:
- a first staple support in the third row of staple cavities;
- a second staple support in the second row of staple cavities distal to the first staple support; and
- a third staple support in the third row of staple cavities distal to the second staple support.

16. The staple cartridge of claim 15, further comprising a second staple driver comprising a fourth staple support in the first row of staple cavities, wherein the fourth staple support is laterally aligned with the third staple support.

17. The staple cartridge of claim 16, wherein the fourth staple support is the only staple support of the second staple driver.

18. The staple cartridge of claim 16, further comprising a staple supported by the fourth staple support, wherein the staple supported by the fourth staple support comprises a marker to provide a visual confirmation to a user that the staple cartridge has completely fired.

19. The staple cartridge of claim 15, further comprising a second staple driver configured to deploy staples from the first row of staple cavities, the second row of staple cavities, and the third row of staple cavities, wherein the second staple driver comprises:
- a fourth staple support in the third row of staple cavities;
- a fifth staple support in the second row of staple cavities distal to the fourth staple support; and
- a sixth staple support in the first row of staple cavities distal to the fifth staple support.

20. The staple cartridge of claim 19, wherein the sixth staple support is laterally aligned with the first staple support.

* * * * *